US009579208B2

(12) United States Patent
Katrana et al.

(10) Patent No.: US 9,579,208 B2
(45) Date of Patent: Feb. 28, 2017

(54) MODULAR RADIAL HEAD PROSTHESIS

(71) Applicant: Biomet Manufacturing, LLC, Warsaw, IN (US)

(72) Inventors: Nicholas J. Katrana, Fort Wayne, IN (US); Thomas M. Vanasse, Warsaw, IN (US); Adam Finley, Leesburg, IN (US); William J. Hamman, Winona Lake, IN (US); Robert Metzger, Wakarusa, IN (US); Bryce A. Isch, Bluffton, IN (US); Christopher H. Martin, Salt Lake City, UT (US)

(73) Assignee: Biomet Manufacturing, LLC, Warsaw, IN (US)

( * ) Notice: Subject to any disclaimer, the term of this patent is extended or adjusted under 35 U.S.C. 154(b) by 52 days.

(21) Appl. No.: 14/541,548

(22) Filed: Nov. 14, 2014

(65) Prior Publication Data

US 2015/0073561 A1    Mar. 12, 2015

Related U.S. Application Data

(60) Division of application No. 12/794,196, filed on Jun. 4, 2010, now Pat. No. 8,920,509, which is a (Continued)

(51) Int. Cl.
*A61F 2/38* (2006.01)
*A61F 2/46* (2006.01)
*A61F 2/30* (2006.01)

(52) U.S. Cl.
CPC .......... *A61F 2/3804* (2013.01); *A61F 2/4637* (2013.01); *A61F 2002/30387* (2013.01);
(Continued)

(58) Field of Classification Search
CPC .................. A61F 2/3804; A61F 2/4637; A61F 2002/30387
See application file for complete search history.

(56) References Cited

U.S. PATENT DOCUMENTS 2,682,265 A    6/1954   Collison
2,719,522 A    10/1955  Hudack
(Continued)

FOREIGN PATENT DOCUMENTS

DE    3205577 A1   10/1982
DE    3605630      9/1987
(Continued)

OTHER PUBLICATIONS

Final Office Action for U.S. Appl. No. 10/999,297, mailed Jun. 9, 2011.
(Continued)

*Primary Examiner* — Bruce E Snow
*Assistant Examiner* — Melissa Hoban
(74) *Attorney, Agent, or Firm* — Schwegman Lundberg & Woessner, P.A.

(57) ABSTRACT

A method for implanting a prosthesis system for replacement of a head portion of a proximal radius includes determining a distance between a proximal radius and a humerus. The method also includes selecting one of a first head component or a second head component based on the determination. The first and second head components have unique heights. The method further includes connecting the selected first or second head component to an articulation component and connecting a stem component to the selected first or second head component.

6 Claims, 25 Drawing Sheets

Related U.S. Application Data continuation-in-part of application No. 12/578,052, filed on Oct. 13, 2009, now Pat. No. 8,425,615, which is a continuation of application No. 10/999,297, filed on Nov. 29, 2004, now Pat. No. 8,114,163, which is a continuation-in-part of application No. 10/464,043, filed on Jun. 18, 2003, now abandoned, which is a continuation of application No. 09/828,745, filed on Apr. 9, 2001, now Pat. No. 6,656,225.

(60) Provisional application No. 60/195,444, filed on Apr. 10, 2000.

(52) U.S. Cl.
CPC ............ *A61F 2002/30604* (2013.01); *A61F 2002/3827* (2013.01); *A61F 2220/0025* (2013.01)

(56) References Cited

U.S. PATENT DOCUMENTS

| | | |
|---|---|---|
| 2,765,787 A | 10/1956 | Pellet |
| 2,781,758 A | 2/1957 | Chevalier |
| 2,785,673 A | 3/1957 | Anderson |
| 3,064,645 A | 11/1962 | Ficat et al. |
| 3,067,740 A | 12/1962 | Haboush |
| 3,102,536 A | 9/1963 | Rose et al. |
| 3,658,056 A | 4/1972 | Huggler et al. |
| 3,670,724 A | 6/1972 | Bosacco |
| 3,694,820 A | 10/1972 | Scales et al. |
| 3,782,373 A | 1/1974 | Smythe |
| 3,806,957 A | 4/1974 | Shersher |
| 3,814,089 A | 6/1974 | Deyerle |
| 3,818,512 A | 6/1974 | Shersher |
| 3,852,830 A | 12/1974 | Marmor |
| 3,859,669 A | 1/1975 | Shersher |
| 3,863,273 A | 2/1975 | Averill |
| 3,874,003 A | 4/1975 | Moser et al. |
| 3,906,550 A | 9/1975 | Rostoker et al. |
| 3,916,451 A | 11/1975 | Buechel et al. |
| 3,918,441 A | 11/1975 | Getscher |
| 3,974,527 A | 8/1976 | Shersher |
| 3,979,778 A | 9/1976 | Stroot |
| 3,987,499 A | 10/1976 | Scharbach et al. |
| 4,004,300 A | 1/1977 | English |
| 4,030,143 A | 6/1977 | Elloy et al. |
| 4,040,131 A | 8/1977 | Gristina |
| 4,042,980 A | 8/1977 | Swanson et al. |
| 4,051,559 A | 10/1977 | Pifferi |
| 4,052,917 A | 10/1977 | Gee |
| 4,079,469 A | 3/1978 | Wadsworth |
| 4,115,875 A | 9/1978 | Rambert et al. |
| 4,129,902 A | 12/1978 | Harmon |
| 4,131,956 A | 1/1979 | Treace |
| 4,219,893 A | 9/1980 | Noiles |
| 4,242,758 A | 1/1981 | Amis et al. |
| 4,245,360 A | 1/1981 | Brinckmann et al. |
| 4,257,129 A * | 3/1981 | Volz .................. A61F 2/389 623/20.33 |
| 4,261,062 A | 4/1981 | Amstutz et al. |
| 4,280,231 A | 7/1981 | Swanson |
| 4,301,552 A | 11/1981 | London |
| 4,301,553 A | 11/1981 | Noiles |
| 4,378,607 A | 4/1983 | Wadsworth |
| 4,383,337 A | 5/1983 | Volz et al. |
| 4,404,691 A | 9/1983 | Buning et al. |
| 4,406,023 A | 9/1983 | Harris |
| 4,407,022 A | 10/1983 | Heimke et al. |
| 4,430,761 A | 2/1984 | Niederer et al. |
| 4,459,708 A | 7/1984 | Buttazzoni |
| 4,488,319 A | 12/1984 | von Recum |
| 4,521,924 A | 6/1985 | Jacobsen et al. |
| 4,532,660 A | 8/1985 | Field |
| 4,550,450 A | 11/1985 | Kinnett |
| 4,578,081 A | 3/1986 | Harder et al. |
| 4,624,674 A | 11/1986 | Pappas et al. |
| 4,645,506 A | 2/1987 | Link |
| 4,655,778 A | 4/1987 | Koeneman |
| 4,658,808 A | 4/1987 | Link |
| 4,676,797 A | 6/1987 | Anapliotis et al. |
| 4,686,978 A | 8/1987 | Wadsworth |
| 4,687,486 A | 8/1987 | Brinckmann et al. |
| 4,693,723 A | 9/1987 | Gabard |
| 4,693,724 A | 9/1987 | Rhenter et al. |
| 4,698,063 A | 10/1987 | Link et al. |
| 4,728,333 A | 3/1988 | Masse et al. |
| 4,764,171 A | 8/1988 | Harder et al. |
| 4,769,040 A | 9/1988 | Wevers |
| 4,770,852 A | 9/1988 | Takahara et al. |
| 4,790,854 A | 12/1988 | Harder et al. |
| 4,822,366 A | 4/1989 | Bolesky |
| 4,822,370 A | 4/1989 | Schelhas |
| 4,827,919 A | 5/1989 | Barbarito et al. |
| 4,834,758 A | 5/1989 | Lane et al. |
| 4,840,632 A | 6/1989 | Kampner |
| 4,842,606 A | 6/1989 | Kranz et al. |
| 4,865,605 A | 9/1989 | Dines et al. |
| 4,865,609 A | 9/1989 | Roche |
| 4,871,369 A | 10/1989 | Muller |
| 4,878,917 A | 11/1989 | Kranz et al. |
| 4,883,489 A | 11/1989 | Grundei et al. |
| 4,895,572 A | 1/1990 | Chernoff |
| 4,904,266 A | 2/1990 | Barber |
| 4,908,032 A | 3/1990 | Keller |
| 4,908,034 A | 3/1990 | Weightman et al. |
| 4,919,669 A | 4/1990 | Lannelongue |
| 4,919,670 A | 4/1990 | Dale et al. |
| 4,919,678 A | 4/1990 | Kranz |
| 4,921,500 A | 5/1990 | Averill et al. |
| 4,923,472 A | 5/1990 | Ugolini |
| 4,932,974 A | 6/1990 | Pappas et al. |
| 4,938,772 A | 7/1990 | Frey et al. |
| 4,938,773 A | 7/1990 | Strand |
| 4,944,757 A | 7/1990 | Martinez et al. |
| 4,950,298 A | 8/1990 | Gustilo et al. |
| 4,963,152 A | 10/1990 | Hofmann et al. |
| 4,963,155 A | 10/1990 | Lazzeri et al. |
| 4,978,357 A | 12/1990 | Goymann et al. |
| 4,979,957 A | 12/1990 | Hodorek |
| 4,985,037 A | 1/1991 | Petersen |
| 4,986,833 A | 1/1991 | Worland |
| 4,995,883 A | 2/1991 | Demane et al. |
| 4,997,444 A | 3/1991 | Farling |
| 5,002,578 A | 3/1991 | Luman |
| 5,002,580 A | 3/1991 | Noble et al. |
| 5,002,581 A | 3/1991 | Paxson et al. |
| 5,007,933 A | 4/1991 | Sidebotham et al. |
| 5,015,257 A | 5/1991 | Crowninshield et al. |
| 5,019,103 A | 5/1991 | Van Zile et al. |
| 5,019,108 A | 5/1991 | Bertin et al. |
| 5,030,234 A | 7/1991 | Pappas et al. |
| 5,030,237 A | 7/1991 | Sorbie et al. |
| 5,032,130 A | 7/1991 | Schelhas et al. |
| 5,035,717 A | 7/1991 | Brooks |
| 5,061,271 A | 10/1991 | Van Zile |
| 5,066,304 A | 11/1991 | Crowninshield et al. |
| 5,071,435 A | 12/1991 | Fuchs et al. |
| 5,074,879 A | 12/1991 | Pappas et al. |
| 5,080,676 A | 1/1992 | May |
| 5,080,685 A | 1/1992 | Bolesky et al. |
| 5,108,437 A | 4/1992 | Kenna |
| 5,108,451 A | 4/1992 | Forte |
| 5,108,452 A | 4/1992 | DeMane et al. |
| 5,116,379 A | 5/1992 | McLardy-Smith |
| 5,135,529 A | 8/1992 | Paxson et al. |
| 5,139,529 A | 8/1992 | Seita et al. |
| 5,147,386 A | 9/1992 | Carignan et al. |
| 5,147,406 A | 9/1992 | Houston et al. |
| 5,152,796 A | 10/1992 | Slamin |
| 5,156,627 A | 10/1992 | Amstutz et al. |
| 5,163,961 A | 11/1992 | Harwin |
| 5,169,401 A | 12/1992 | Lester et al. |
| 5,181,925 A | 1/1993 | Houston et al. |

(56) References Cited

U.S. PATENT DOCUMENTS

| | | |
|---|---|---|
| 5,181,928 A | 1/1993 | Bolesky et al. |
| 5,192,320 A | 3/1993 | Anazawa et al. |
| 5,194,066 A | 3/1993 | Van Zile |
| 5,201,768 A | 4/1993 | Caspari et al. |
| 5,201,769 A | 4/1993 | Schutzer |
| 5,201,881 A | 4/1993 | Evans |
| 5,201,882 A | 4/1993 | Paxson |
| 5,207,682 A | 5/1993 | Cripe |
| 5,207,711 A | 5/1993 | Caspari et al. |
| 5,211,666 A | 5/1993 | Fetto |
| 5,219,362 A | 6/1993 | Tuke et al. |
| 5,246,459 A | 9/1993 | Elias |
| 5,261,915 A | 11/1993 | Durlacher et al. |
| 5,271,737 A | 12/1993 | Baldwin et al. |
| 5,282,865 A | 2/1994 | Dong |
| 5,286,260 A | 2/1994 | Bolesky et al. |
| 5,290,313 A | 3/1994 | Heldreth |
| 5,314,479 A | 5/1994 | Rockwood, Jr. et al. |
| 5,314,494 A | 5/1994 | Huiskes et al. |
| 5,316,550 A | 5/1994 | Forte |
| 5,326,363 A | 7/1994 | Aikins |
| 5,326,368 A | 7/1994 | Collazo |
| 5,330,534 A | 7/1994 | Herrington et al. |
| 5,336,266 A | 8/1994 | Caspari et al. |
| 5,336,268 A | 8/1994 | Rispeter |
| 5,342,363 A | 8/1994 | Richelsoph |
| 5,344,461 A | 9/1994 | Phlipot |
| 5,358,526 A | 10/1994 | Tornier |
| 5,358,527 A | 10/1994 | Forte |
| 5,358,529 A | 10/1994 | Davidson |
| 5,358,534 A | 10/1994 | Dudasik et al. |
| 5,370,699 A | 12/1994 | Hood et al. |
| 5,370,701 A | 12/1994 | Finn |
| 5,370,706 A | 12/1994 | Bolesky et al. |
| 5,395,401 A | 3/1995 | Bahler |
| 5,397,360 A | 3/1995 | Cohen et al. |
| 5,405,394 A | 4/1995 | Davidson |
| 5,405,395 A | 4/1995 | Coates |
| 5,405,403 A | 4/1995 | Mikhail |
| 5,413,605 A | 5/1995 | Ashby et al. |
| 5,425,777 A | 6/1995 | Sarkisian et al. |
| 5,425,779 A | 6/1995 | Schlosser et al. |
| 5,431,658 A | 7/1995 | Moskovich |
| 5,443,512 A | 8/1995 | Parr et al. |
| 5,458,637 A | 10/1995 | Hayes |
| 5,458,644 A | 10/1995 | Grundei |
| 5,458,651 A | 10/1995 | Lawes |
| 5,480,443 A | 1/1996 | Elias |
| 5,480,453 A | 1/1996 | Burke |
| 5,489,309 A | 2/1996 | Lackey et al. |
| 5,489,310 A | 2/1996 | Mikhail |
| 5,507,817 A | 4/1996 | Craig et al. |
| 5,507,818 A | 4/1996 | McLaughlin |
| 5,507,822 A | 4/1996 | Bouchon et al. |
| 5,507,827 A | 4/1996 | Grundei et al. |
| 5,507,830 A | 4/1996 | DeMane et al. |
| 5,507,832 A | 4/1996 | Michielli et al. |
| 5,507,833 A | 4/1996 | Bohn |
| 5,509,935 A | 4/1996 | Fosco et al. |
| 5,549,682 A | 8/1996 | Roy |
| 5,549,686 A | 8/1996 | Johnson et al. |
| 5,549,687 A | 8/1996 | Coates et al. |
| 5,549,702 A | 8/1996 | Ries et al. |
| 5,549,703 A | 8/1996 | Daigle et al. |
| 5,549,705 A | 8/1996 | Michielli et al. |
| 5,549,706 A | 8/1996 | McCarthy |
| 5,554,192 A | 9/1996 | Crowninshield |
| 5,556,433 A | 9/1996 | Gabriel et al. |
| 5,571,193 A | 11/1996 | Kampner |
| 5,580,352 A | 12/1996 | Sekel |
| 5,591,233 A | 1/1997 | Kelman et al. |
| 5,593,449 A | 1/1997 | Roberson, Jr. |
| 5,609,641 A | 3/1997 | Johnson et al. |
| 5,609,645 A | 3/1997 | Vinciguerra |
| 5,645,607 A | 7/1997 | Hickey |
| 5,653,764 A | 8/1997 | Murphy |
| 5,653,765 A | 8/1997 | McTighe et al. |
| 5,658,340 A | 8/1997 | Muller et al. |
| 5,658,344 A | 8/1997 | Hurlburt |
| 5,658,352 A | 8/1997 | Draenert |
| 5,683,469 A | 11/1997 | Johnson et al. |
| 5,683,472 A | 11/1997 | O'Neil et al. |
| 5,697,977 A | 12/1997 | Pisharodi |
| 5,702,457 A | 12/1997 | Walch et al. |
| 5,702,460 A | 12/1997 | Carls et al. |
| 5,702,463 A | 12/1997 | Pothier et al. |
| 5,702,464 A | 12/1997 | Lackey et al. |
| 5,702,480 A | 12/1997 | Kropf et al. |
| 5,702,484 A | 12/1997 | Goymann et al. |
| 5,702,485 A | 12/1997 | Burke et al. |
| 5,702,486 A | 12/1997 | Craig et al. |
| 5,713,901 A * | 2/1998 | Tock ............ A61B 17/72 606/151 |
| 5,725,587 A | 3/1998 | Garber |
| 5,725,592 A | 3/1998 | White et al. |
| 5,725,594 A | 3/1998 | McTighe et al. |
| 5,725,595 A | 3/1998 | Gustilo |
| 5,725,596 A | 3/1998 | Burke |
| 5,728,163 A | 3/1998 | Maksene |
| 5,746,771 A | 5/1998 | Clement, Jr. et al. |
| 5,755,800 A | 5/1998 | O'Neil et al. |
| 5,755,803 A | 5/1998 | Haines et al. |
| 5,755,805 A | 5/1998 | Whiteside |
| 5,755,807 A | 5/1998 | Anstaett et al. |
| 5,755,811 A | 5/1998 | Tanamal et al. |
| 5,766,255 A | 6/1998 | Slamin et al. |
| 5,766,261 A | 6/1998 | Neal et al. |
| 5,769,093 A | 6/1998 | Bays |
| 5,776,194 A | 7/1998 | Mikol et al. |
| 5,776,200 A | 7/1998 | Johnson et al. |
| 5,776,201 A | 7/1998 | Colleran et al. |
| 5,776,204 A | 7/1998 | Noble et al. |
| 5,782,920 A | 7/1998 | Colleran |
| 5,782,921 A | 7/1998 | Colleran et al. |
| 5,782,922 A | 7/1998 | Vandewalle |
| 5,800,552 A | 9/1998 | Forte |
| 5,800,558 A | 9/1998 | LaHaise, Sr. |
| 5,800,560 A | 9/1998 | Draenert |
| 5,824,096 A | 10/1998 | Pappas et al. |
| 5,824,097 A | 10/1998 | Gabriel et al. |
| 5,855,619 A | 1/1999 | Caplan et al. |
| 5,858,020 A | 1/1999 | Johnson et al. |
| 5,860,969 A | 1/1999 | White et al. |
| 5,863,297 A | 1/1999 | Walter et al. |
| 5,871,541 A | 2/1999 | Gerber |
| 5,871,547 A | 2/1999 | Abouaf et al. |
| 5,871,548 A | 2/1999 | Sanders et al. |
| 5,876,459 A | 3/1999 | Powell |
| 5,879,391 A | 3/1999 | Slamin |
| 5,879,393 A | 3/1999 | Whiteside et al. |
| 5,879,394 A | 3/1999 | Ashby et al. |
| 5,879,395 A | 3/1999 | Tornier et al. |
| 5,888,203 A | 3/1999 | Goldberg |
| 5,888,208 A | 3/1999 | Ro |
| 5,888,245 A | 3/1999 | Meulink et al. |
| 5,902,340 A | 5/1999 | White et al. |
| 5,906,210 A | 5/1999 | Herbert |
| 5,906,644 A | 5/1999 | Powell |
| 5,928,285 A | 7/1999 | Bigliani et al. |
| 5,928,286 A | 7/1999 | Ashby et al. |
| 5,928,289 A | 7/1999 | Deckner |
| 5,931,871 A | 8/1999 | Baur et al. |
| 5,935,172 A | 8/1999 | Ochoa et al. |
| 5,944,756 A | 8/1999 | Fischetti et al. |
| 5,944,758 A | 8/1999 | Mansat et al. |
| 5,951,606 A | 9/1999 | Burke |
| 5,961,555 A * | 10/1999 | Huebner ............ A61F 2/40 623/19.11 |
| 5,972,033 A | 10/1999 | Drouin et al. |
| 5,976,178 A | 11/1999 | Goldsteen et al. |
| 5,981,828 A | 11/1999 | Nelson et al. |
| 5,997,577 A | 12/1999 | Herrington et al. |
| 6,004,352 A | 12/1999 | Buni |
| 6,007,581 A | 12/1999 | Noble et al. |

(56) References Cited

U.S. PATENT DOCUMENTS

| | | |
|---|---|---|
| 6,010,535 A | 1/2000 | Shah |
| 6,013,104 A | 1/2000 | Kampner |
| 6,015,431 A | 1/2000 | Thornton et al. |
| 6,015,437 A | 1/2000 | Stossel |
| 6,045,581 A | 4/2000 | Burkinshaw |
| 6,045,582 A | 4/2000 | Prybyla |
| 6,162,253 A | 12/2000 | Conzemius et al. |
| 6,168,630 B1* | 1/2001 | Keller .................. A61F 2/4261 623/21.11 |
| 6,214,014 B1 | 4/2001 | McGann |
| 6,214,053 B1 | 4/2001 | Ling et al. |
| 6,217,616 B1* | 4/2001 | Ogilvie ................ A61F 2/3804 623/20.11 |
| 6,270,529 B1* | 8/2001 | Terrill-Grisoni ...... A61F 2/3804 623/18.11 |
| 6,277,123 B1 | 8/2001 | Maroney et al. |
| 6,306,171 B1 | 10/2001 | Conzemius |
| 6,319,286 B1 | 11/2001 | Fernandez et al. |
| 6,352,560 B1 | 3/2002 | Poeschmann et al. |
| 6,361,563 B2 | 3/2002 | Terrill-Grisoni et al. |
| 6,361,566 B1 | 3/2002 | Al-Hafez |
| 6,379,387 B1 | 4/2002 | Tornier |
| 6,383,223 B1 | 5/2002 | Baehler et al. |
| 6,432,110 B1 | 8/2002 | Richelsoph |
| 6,440,142 B1 | 8/2002 | Ralph et al. |
| 6,494,913 B1 | 12/2002 | Huebner |
| 6,527,775 B1 | 3/2003 | Warburton |
| 6,589,282 B2 | 7/2003 | Pearl |
| 6,603,638 B2 | 8/2003 | Yotsuya |
| 6,613,092 B1 | 9/2003 | Kana et al. |
| 6,656,225 B2 | 12/2003 | Martin |
| 6,709,459 B1 | 3/2004 | Cooney, III et al. |
| 6,942,699 B2 | 9/2005 | Stone et al. |
| 7,153,310 B2 | 12/2006 | Ralph et al. |
| 7,179,259 B1 | 2/2007 | Gibbs |
| 7,297,163 B2 | 11/2007 | Huebner |
| 7,404,795 B2 | 7/2008 | Ralph et al. |
| 7,462,182 B2 | 12/2008 | Lim |
| 7,507,255 B2 | 3/2009 | Ralph et al. |
| 7,534,266 B2 | 5/2009 | Kluger |
| 7,559,941 B2 | 7/2009 | Zannis et al. |
| 7,575,580 B2 | 8/2009 | Lim et al. |
| 7,637,952 B2 | 12/2009 | Landry et al. |
| 7,666,189 B2 | 2/2010 | Gerber et al. |
| 7,722,675 B2 | 5/2010 | Ralph et al. |
| 7,749,252 B2 | 7/2010 | Zucherman et al. |
| 7,749,269 B2 | 7/2010 | Peterman et al. |
| 7,758,584 B2 | 7/2010 | Bankoski et al. |
| 7,763,031 B2 | 7/2010 | Tulkis |
| 8,110,005 B2 | 2/2012 | Berelsman et al. |
| 8,114,163 B2 | 2/2012 | Berelsman et al. |
| 8,366,781 B2 | 2/2013 | Berelsman et al. |
| 8,425,615 B2 | 4/2013 | Berelsman et al. |
| 8,535,382 B2 | 9/2013 | Kehres et al. |
| 8,920,509 B2* | 12/2014 | Katrana ................ A61F 2/3804 623/21.12 |
| 9,333,084 B2 | 5/2016 | Berelsman et al. |
| 2001/0037154 A1 | 11/2001 | Martin |
| 2001/0053935 A1* | 12/2001 | Hartdegen ............ A61F 2/4684 623/19.12 |
| 2003/0149485 A1 | 8/2003 | Tornier |
| 2003/0212457 A1 | 11/2003 | Martin |
| 2004/0254581 A1 | 12/2004 | Leclair |
| 2005/0075735 A1 | 4/2005 | Berelsman et al. |
| 2005/0171613 A1 | 8/2005 | Sartorius et al. |
| 2005/0216090 A1 | 9/2005 | O'Driscoll et al. |
| 2005/0246027 A1 | 11/2005 | Metzger et al. |
| 2006/0195196 A1 | 8/2006 | Pendleton et al. |
| 2009/0118837 A1 | 5/2009 | Winslow et al. |
| 2009/0125115 A1 | 5/2009 | Popoola et al. |
| 2010/0030339 A1 | 2/2010 | Berelsman et al. |
| 2010/0262252 A1 | 10/2010 | Berelsman et al. |
| 2010/0312349 A1 | 12/2010 | Berelsman et al. |
| 2012/0109323 A1 | 5/2012 | Berelsman et al. |
| 2013/0333198 A1 | 12/2013 | Kehres et al. |

FOREIGN PATENT DOCUMENTS

| | | |
|---|---|---|
| DE | 4230438 A1 | 3/1993 |
| DE | 009300791 | 7/1993 |
| DE | 4320086 A1 | 12/1994 |
| DE | 69304936 T2 | 2/1997 |
| DE | 19722389 A1 | 12/1998 |
| DE | 19548154 A1 | 9/2002 |
| EP | 0000549 A1 | 2/1979 |
| EP | 0163121 A1 | 12/1985 |
| EP | 0278807 A2 | 8/1988 |
| EP | 0325566 A2 | 7/1989 |
| EP | 0390883 A1 | 10/1990 |
| EP | 0474320 A1 | 3/1992 |
| EP | 0531263 A1 | 3/1993 |
| EP | 0538895 A2 | 4/1993 |
| EP | 0549480 A1 | 6/1993 |
| EP | 0552950 A1 | 7/1993 |
| EP | 0617933 A1 | 10/1994 |
| EP | 0645126 A2 | 3/1995 |
| EP | 0683649 A1 | 11/1995 |
| EP | 0689808 A1 | 1/1996 |
| EP | 0809986 A2 | 12/1997 |
| EP | 1051954 A1 | 11/2000 |
| FR | 2519248 A1 | 7/1983 |
| FR | 2619502 A1 | 2/1989 |
| FR | 2632516 A1 | 12/1989 |
| FR | 2682031 A1 | 4/1993 |
| FR | 2689756 A1 | 10/1993 |
| FR | 2720626 A1 | 12/1995 |
| FR | 2721820 A1 | 1/1996 |
| GB | 2253147 A | 9/1992 |
| GB | 2334090 A | 8/1999 |
| GB | 2334890 A | 9/1999 |
| WO | 8302555 A1 | 8/1983 |
| WO | 9002533 A2 | 3/1990 |
| WO | 9118559 A1 | 12/1991 |
| WO | 9417757 A1 | 8/1994 |
| WO | 9600538 A1 | 1/1996 |
| WO | 9625123 A2 | 8/1996 |
| WO | 9716137 A1 | 5/1997 |

OTHER PUBLICATIONS

Final Office Action for U.S. Appl. No. 10/999,297, mailed Dec. 3, 2009.

Non-Final Office Action for U.S. Appl. No. 10/999,297, mailed Mar. 11, 2009.

Non-Final Office Action for U.S. Appl. No. 10/999,297, mailed Dec. 22, 2010.

Non-Final Office Action for U.S. Appl. No. 13/041,864, mailed Jun. 10, 2011.

"rHead.TM. Lateral Surgical Technique Insert," brochure. Jul. 2007. SBI Small Bone Innovations.

"The Morrey Treatment Algorithm for Elbow Management," brochure. Aug. 2008. SBI Small Bone Innovations, Inc. (2 sheets).

"Uni-Elbow PGT.TM., Surgical Technique," brochure. 2006. SBI Small Bone Innovations, Inc. (6 sheets).

"Uni-Elbow.TM. Radio Capitellum Implant for Uni-Compartmental Arthroplasty," brochure. 2009. SBI Small Bone Innovations, Inc. (2 sheets).

Biomet Merck, "Liverpool Radial Head Replacement" brochure, 2001 (6 pages).

Biomet, Orthopedics, Inc., "Liverpool.TM. Radial Head Replacement, Operative Technique" brochure, 2002 (6 pages).

Finkemeier, Chrristopher, M.D., and Olmstead, Stephen, M.D., Drawing dated Mar. 5, 1999 and related Expired Confidential Disclosure Agreement dated Feb. 23, 1999.

Morrey, B.F., M.D., "Radial Head Fracture," The Elbow and its Disorders, pp. 355-381, Chapter 20, The Mayo Foundation (1985).

Non-Final Office Action for U.S. Appl. No. 12/827,568, mailed Apr. 6, 2012.

(56) References Cited

OTHER PUBLICATIONS

Non-Final Office Action for U.S. Appl. No. 12/578,052, mailed Jul. 24, 2012.

Non-Final Office Action for U.S. Appl. No. 13/324,328, mailed Dec. 3, 2012.

"U.S. Appl. No. 12/794,196, Examiner Interview Summary mailed Jan. 11, 2013", 3 pgs.

"U.S. Appl. No. 12/794,196, Final Office Action mailed Nov. 26, 2012", 11 pgs.

"U.S. Appl. No. 12/794,196, Non Final Office Action mailed Jun. 21, 2012", 12 pgs.

"U.S. Appl. No. 12/794,196, Notice of Allowance mailed Aug. 21, 2014", 5 pgs.

"U.S. Appl. No. 12/794,196, Response filed Jan. 17, 2013 to Final Office Action mailed Nov. 26, 2012", 12 pgs.

"U.S. Appl. No. 12/794,196, Response filed Apr. 19, 2012 to Restriction Requirement mailed Mar. 19, 2012", 10 pgs.

"U.S. Appl. No. 12/794,196, Response filed Jun. 4, 2012 to Restriction Requirement mailed May 7, 2012", 7 pgs.

"U.S. Appl. No. 12/794,196, Response filed Sep. 17, 2012 to Non Final Office Action mailed Jun. 21, 2012", 11 pgs.

"U.S. Appl. No. 12/794,196, Restriction Requirement mailed Mar. 19, 2012", 10 pgs.

"U.S. Appl. No. 12/794,196, Restriction Requirement mailed May 7, 2012", 6 pgs.

"U.S. Appl. No. 13/041,864, Appeal Decision mailed Jul. 23, 2015", 12 pgs.

"U.S. Appl. No. 13/343,991, Final Office Action mailed Oct. 16, 2015", 5 pgs.

"U.S. Appl. No. 13/343,991, Non Final Office Action mailed Apr. 9, 2015", 10 pgs.

"U.S. Appl. No. 13/343,991, Notice of Allowance mailed Jan. 6, 2016", 5 pgs.

"U.S. Appl. No. 13/343,991, Response filed Jul. 9, 2015 to Non Final Office Action mailed Apr. 9, 2015", 11 pgs.

"U.S. Appl. No. 13/343,991, Response filed Dec. 16, 2015 to Final Office Action mailed Oct. 16, 2015", 8 pgs.

"U.S. Appl. No. 13/968,658, Final Office Action mailed Mar. 9, 2016", 9 pgs.

"U.S. Appl. No. 13/968,658, Non Final Office Action mailed Oct. 7, 2015", 9 pgs.

"U.S. Appl. No. 13/968,658, Response filed Feb. 3, 2016 to Non Final Office Action mailed Oct. 7, 2015", 9 pgs.

"U.S. Appl. No. 13/968,658, Response filed Jun. 9, 2016 to Final Office Action mailed Mar. 9, 2016", 8 pgs.

* cited by examiner

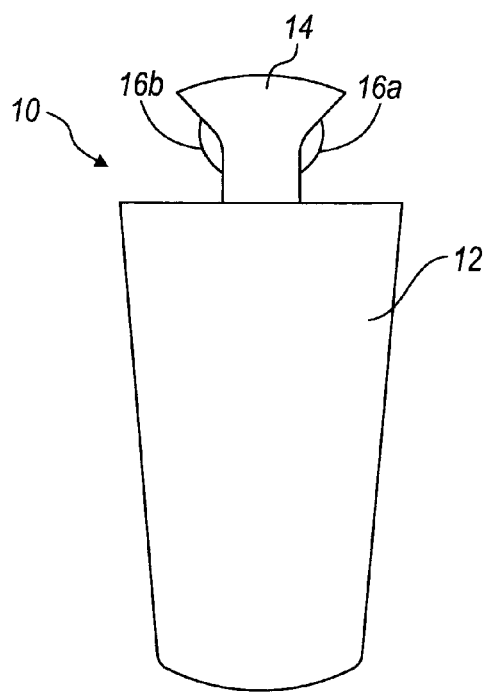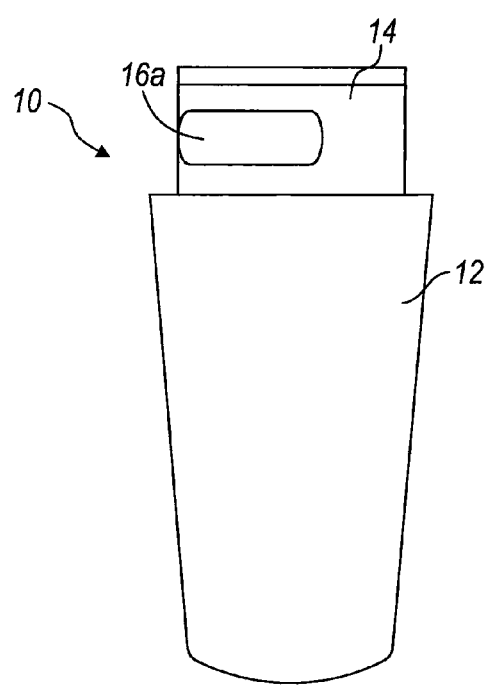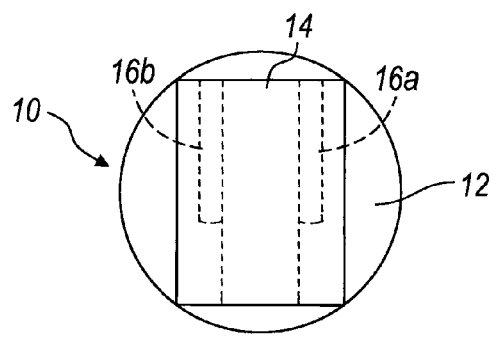

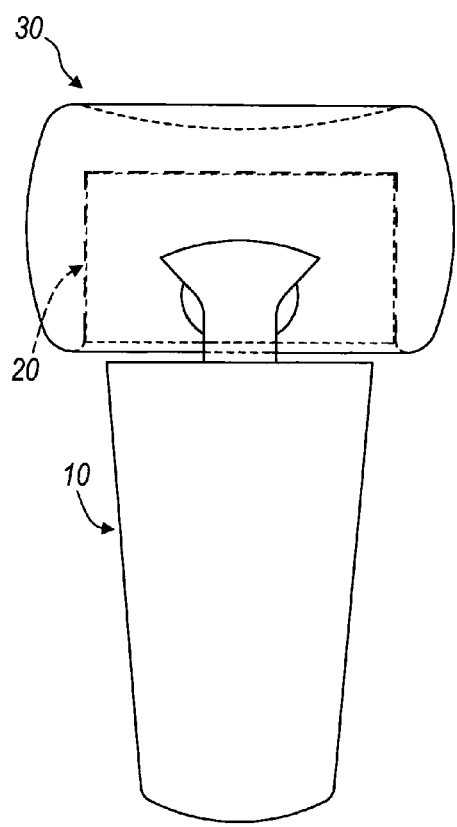
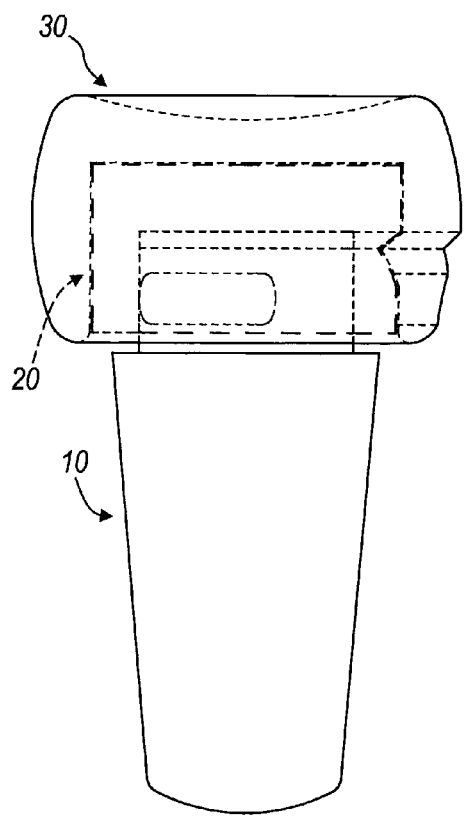
FIG. 11
FIG. 12
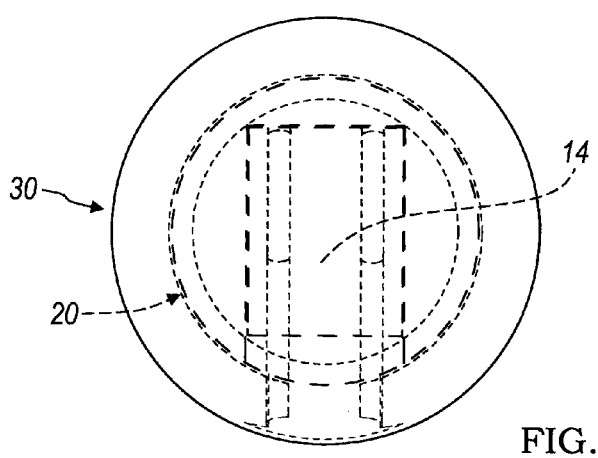
FIG. 13

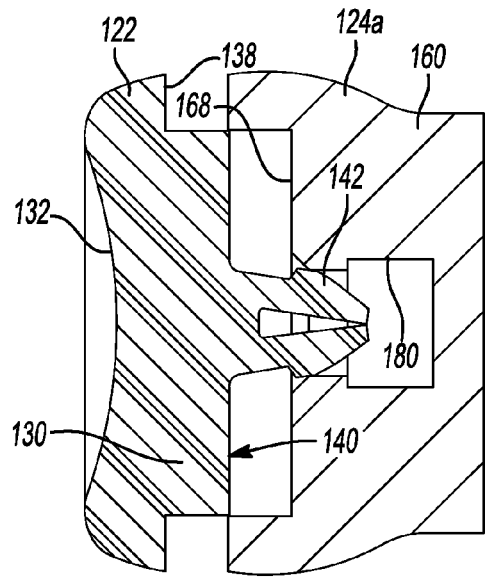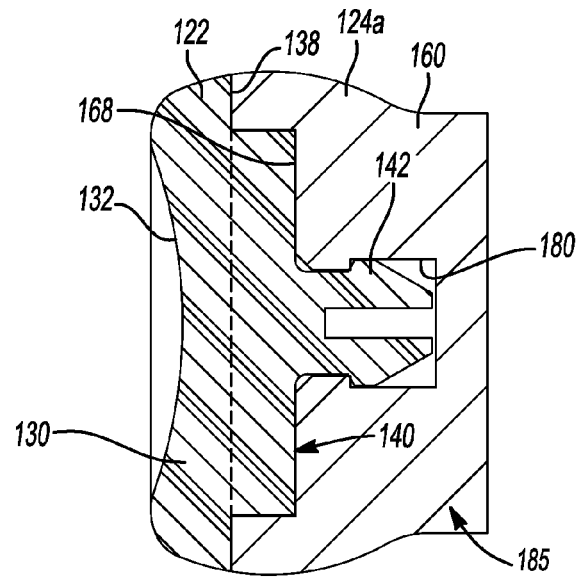
FIG. 32A  FIG. 32B
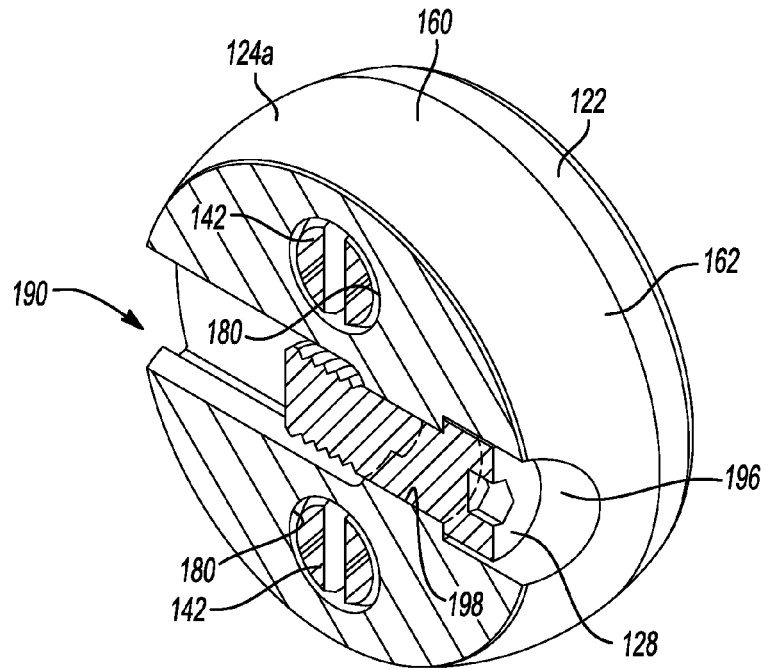
FIG. 33

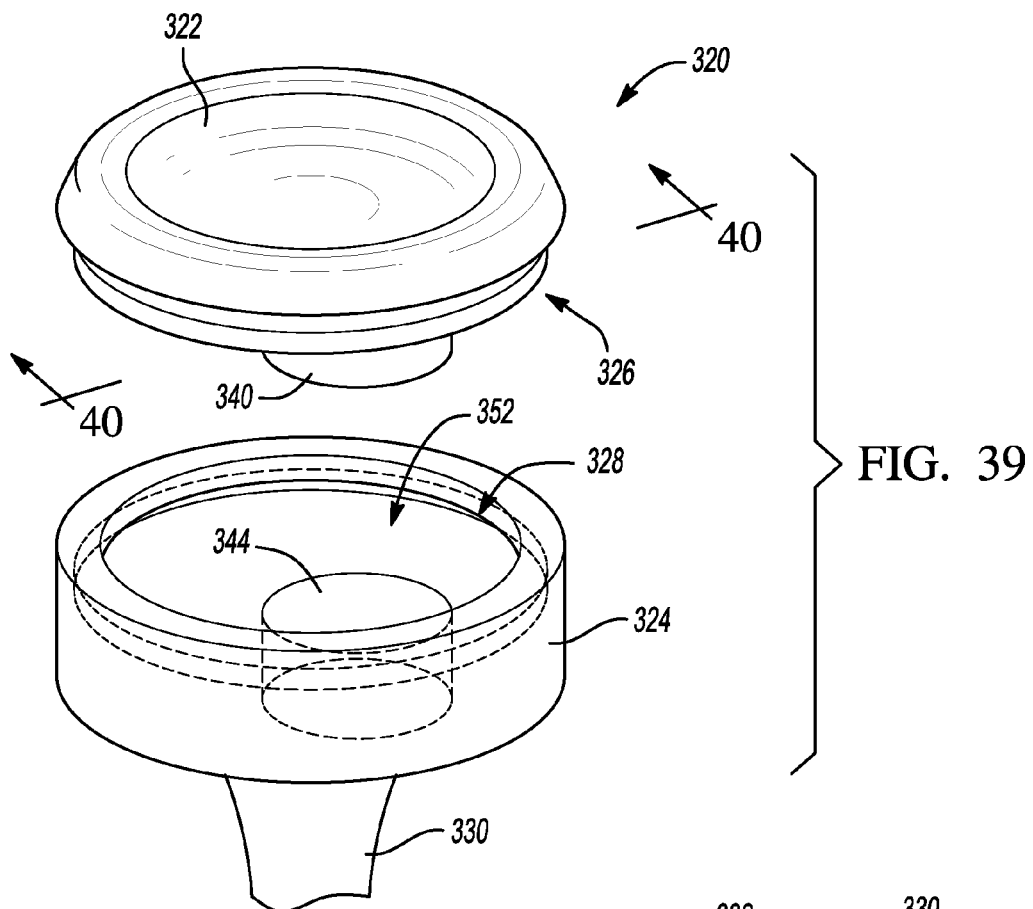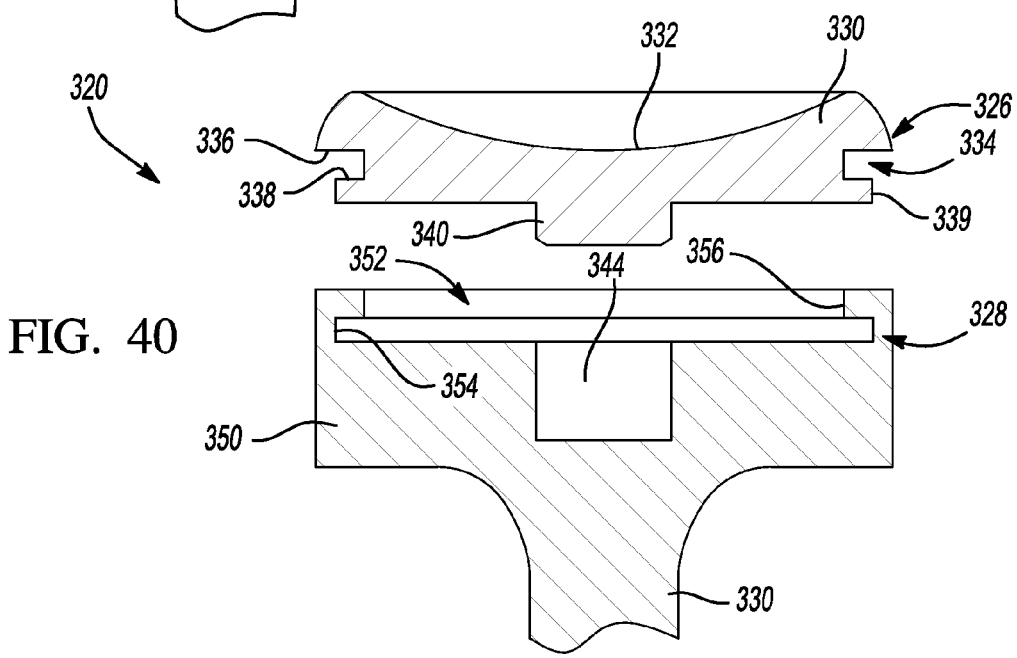

MODULAR RADIAL HEAD PROSTHESIS

CROSS-REFERENCE TO RELATED APPLICATIONS

This application is a divisional of U.S. patent application Ser. No. 12/794,196, filed Jun. 4, 2010, which is a continuation-in-part of U.S. patent application Ser. No. 12/578,052, filed Oct. 13, 2009 (now issued as U.S. Pat. No. 8,425,615 on Apr. 23, 2013), which is a continuation of U.S. patent application Ser. No. 10/999,297, filed Nov. 29, 2004 (now issued as U.S. Pat. No. 8,114,163 on Feb. 14, 2012), which is a continuation-in-part of U.S. patent application Ser. No. 10/464,043, filed on Jun. 18, 2003 (now abandoned), which is a continuation of U.S. patent application Ser. No. 09/828,745, filed Apr. 9, 2001 (now issued as U.S. Pat. No. 6,656,225 on Dec. 2, 2003), which claims the benefit of U.S. Provisional Application 60/195,444, filed Apr. 10, 2000. The disclosures of the above applications and patents are hereby incorporated by reference as fully set forth herein.

FIELD

The present disclosure relates to a humeral implant and more specifically relates to a method and apparatus for adjusting the height and/or the angle of the humeral implant.

BACKGROUND

Trauma to the elbow joint frequently involves damage to the ligamentous support of the elbow and fractures of the osseous structures responsible for the skeletal integrity of the elbow joint. The proximal aspect of the radius, or radial head, is frequently injured either in isolation or in combination with injury to other bony or ligamentous structures of the elbow joint. The radial head may also be fractured in association with injuries to the forearm axis, including disruptions of the interosseous membrane between the radius and the ulna. Whether in isolation or in combination with other injuries, fractures of the radial head can be difficult to treat.

Fractures of the radial head are either reconstructable or unreconstructable. Despite various technical advances in the reconstruction of radial head fractures, a certain percentage of fractures are not amenable to reconstruction due to the degree of comminution or severity of the fracture. In general, unreconstructable radial head fractures result from high energy trauma and are therefore frequently associated with significant injuries to other osseous or ligamentous structures of the elbow joint or forearm. In these cases, restoration of the stabilizing function of the radial head is critical to allow the ligaments of the elbow or forearm to heal in appropriate relationships, thereby restoring stability to the elbow or forearm. This stabilizing function depends, in part, upon re-establishing the appropriate distance between the capitellum and the proximal shaft of the radius.

Prosthetic replacement of the radial head has evolved rather slowly. The first widely used prosthetic radial head was introduced in the 1970's and was composed of silicone. Silicone implants placed in various joints throughout the body led to "silicone synovitis," in which the silicone induced an inflammatory response within the joint. Further, silicone radial head prostheses were found to be incapable of resisting the stresses to which the radial head is subjected, rendering it less useful in stabilizing the injured elbow or forearm.

The difficulties apparent with silicone led to experimentation with metal radial head implants. These prostheses are fashioned from a single piece of metal (often titanium) and include a stem and a head portion. The head portion is shaped to approximate the anatomy of the radial head. These metallic prostheses are capable of resisting the compressive stresses to which the radial head is subjected, as has been demonstrated in several biomechanical studies. However, significant problems remain with these prostheses.

Anatomic and radiographic studies of the dimensions of the radial head reveal a disparity with currently available metallic prostheses. Therefore it has been difficult to restore appropriate anatomic alignments within the elbow. Therefore restoration of the appropriate relationship between the capitellum and proximal shaft of the radius has been very difficult to achieve with these prostheses. Additionally, the fact that these prostheses are fashioned from a single piece of metal has led to technical difficulties with insertion and removal. Surgeons have had difficulty with matching both the size of the stem to the canal of the proximal radius and the size of the head portion to the patient's native radial head. Removal of these non-modular components frequently requires release of the lateral ligaments of the elbow and the annular ligament, which binds the neck of the proximal radius to the proximal ulna. Thus the elbow is frequently destabilized during removal of these prostheses.

Designers of prosthetic joint replacements in the hip, shoulder, knee and fingers have circumvented the above mentioned difficulties by employing the use of modular components. Modularity allows for each aspect of a prosthesis to be sized appropriately to its recipient anatomic site. The concept of modularity has only recently been applied to commercially available radial head prostheses. Currently available modular radial head prostheses employ a mechanism by which the head component is impacted over and onto the stem component. The surgical exposure must therefore allow sufficient room for the head to be maneuvered over the stem prior to being impacted. With impaction, the height of the prosthesis may be decreased, resulting in an increased distance between the capitellum and the proximal end of the radius. Increasing this distance alters the bony anatomy such that the ligaments of the elbow joint are not held in their appropriate lengths and tensions. Instability of the elbow or inappropriate healing of the ligaments may result. Furthermore, removal of these prostheses is accomplished in the same manner as the above mentioned metallic implants, often requiring destabilization of the lateral aspect of the elbow joint.

In order to reap the benefits of modularity in radial head prosthetic replacement, a reliable and surgically appropriate method to secure the stem of the prosthesis to the head of the prosthesis and which allows for accurate restoration of the appropriate spatial relationships between the bones of the elbow is required.

SUMMARY

In accordance with one aspect of the present disclosure, a method for implanting a prosthesis system for replacement of a head portion of a proximal radius is provided. The method can include determining a distance between a proximal radius and a humerus. The method can also include selecting one of a first head component or a second head component based on the determination. The first and second head components can have unique heights. The method can further include connecting the selected first or second head component to an articulation component and connecting a stem component to the selected first or second head component.

In accordance with another aspect of the present disclosure, a method for implanting a prosthesis system for replacement of a head portion of a proximal radius is provided. The method can include determining a distance between a proximal radius and a humerus. The method can also include selecting an articulation component and a head component based on the determination. The articulation component can have a first connection portion. The head component can have a second connection portion. The method can further include reducing a dimension of one of the articulation component or the head component from a first size to a second size. The method can also include advancing one of the articulation component or the head component into contact with the other of the articulation component or head component and returning the dimension to the first size such that the first and second connection portions interlock.

Further areas of applicability of the present disclosure will become apparent from the detailed description provided hereinafter. It should be understood that the detailed description and specific examples, while indicating the preferred embodiment of the disclosure, are intended for purposes of illustration only and are not intended to limit the scope of the disclosure.

BRIEF DESCRIPTION OF THE DRAWINGS

The present disclosure will become more fully understood from the detailed description and the accompanying drawings, wherein:

FIG. 1 is a front view of a stem component;

FIG. 2 is a side view of the stem component from a perspective perpendicular to that of FIG. 1;

FIG. 3 is a top view of the stem component;

FIG. 11 is a front view of an assembled prosthesis;

FIG. 12 is a side view of an assembled prosthesis from a perspective perpendicular to that of FIG. 11;

FIG. 13 is a top view of an assembled prosthesis;

FIGS. 32a and 32b are partial cross-sectional views of the articulation component and head component illustrating an exemplary assembly sequence;

FIG. 33 is a cross-sectional view of the modular radial head prosthesis taken along lines 33-33 of FIG. 29;

FIG. 39 is an exploded perspective view of a head prosthesis system including an articulating component and a head component according to other features of the instant disclosure;

FIG. 40 illustrates a cross-sectional view of the head prosthesis system taken along lines 40-40 of FIG. 39;

DETAILED DESCRIPTION OF THE VARIOUS EMBODIMENTS

Figure 4:
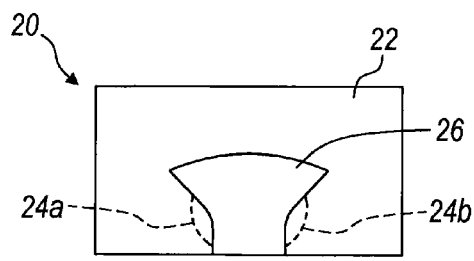
FIG. 4 is a front view of an inner core of a head component.

The following description of the preferred embodiment(s) is merely exemplary in nature and is in no way intended to limit the disclosure, its application or uses.

Before the present disclosure is disclosed and described, it is to be understood that this disclosure is not limited to the particular configurations, process steps and materials disclosed herein as these may vary to some degree. It is also to be understood that the terminology used herein is used for the purpose of describing particular embodiments only, and is not intended to be limiting as the scope of the present disclosure. The disclosure will be limited only by the appended claims and equivalents thereof.

It must be noted that, as used in this specification and the appended claims, singular forms of "a," "an," and "the" include plural referents unless the content clearly dictates otherwise.

"Radial head" is defined as the essentially cylindrical protrusion found at the proximal end of a radius bone. The term "radial head" can also be used to modify or describe the prosthesis of the present disclosure.

"Longitudinal axis" is an imaginary line that is defined by the center of the stem component in the direction of intramedullary canal insertion. Thus, the "longitudinal axis" is also roughly defined as running parallel to a centerline running between the proximal and distal end of the radius bone.

"Transverse axis" or "assembly axis" is an axis that intersects the longitudinal axis. The transverse axis can be linear or non-linear. For example, if non-linear, the axis can be arcuate, provided the assembly axis intersects the longitudinal axis. Thus, angles >0° and <180° qualify as "transverse." However, for practical purposes, the transverse axis can be from 45° to 135° with respect to the longitudinal axis in order to significantly benefit from the modular assembly benefits described herein. In many instances, an essentially perpendicular transverse axis with respect to the longitudinal axis will be present.

"Protuberance" can include any protuberance functional with the present disclosure, particularly with respect to certain locking mechanisms. For example, such protuberances can be convexities.

"Concavity" is intended to describe an open space defined by a mounting portion of a stem component, or an inner core. With respect to a locking mechanism, the concavity can be configured to inversely match and accept a protuberance, though this is not required.

"Intramedullary" shall mean within the marrow cavity of a bone.

"Native" is used to describe the condition of the bone or the head of a bone prior to damage or removal.

For the purposes of promoting an understanding of the principles of the disclosure, reference will now be made to the exemplary embodiments illustrated in the drawings, and specific language will be used to describe the same. It will nevertheless be understood that no limitation of the scope of the disclosure is thereby intended. Any alterations and further modifications of the inventive features illustrated herein, and any additional applications of the principles of the disclosure as illustrated herein, which would occur to one skilled in the relevant art and having possession of this disclosure, are to be considered within the scope of the disclosure.

In order to remedy the shortcomings of prosthetic radial head replacement, a radial head prosthesis is disclosed that enables the assembly without having to significantly remove or manipulate bone and tissue as part of an overhead assembly. By implementing a sliding mechanism for the assembly of the modular radial head prosthesis as described herein, improvement over the commercially available prosthetics can be achieved. Specifically, a sliding mechanism in conjunction with a locking mechanism enables the secure attachment and reasonable removal of a head component from an intact stem component, without the disadvantages associated with head component insertion along the longitudinal axis.

With the above descriptions and definitions in mind, a stem component 10 is shown in FIG. 1. Generally, the stem component 10 comprises an anchoring portion 12 and a mounting portion 14. The anchoring portion 12 is the portion that is anchored within a canal of the proximal radius, providing support to the radial head prosthetic as a whole. In this embodiment, the anchoring portion 12 is tapered and can be coated or textured to allow bone ingrowth after insertion into the radius bone of a patient. The anchoring portion can be cemented, press fit, and/or impacted into the intramedullary canal as is known by those skilled in the art. If a cement is used, then a cement such as, for example, methyl methacrylate, can be used. If desired, various sized broaches (not shown) can be provided such that the surgeon can sound the diameter of the proximal radial shaft, thereby selecting an appropriate sized stem component. In this embodiment, the mounting portion 14 is configured as a dovetail shaped mount when viewed from the front perspective shown in FIG. 1. On each side of the mounting portion 14 are the stem protuberances 16a, 16b. Though not required, the entire stem component 10 (i.e., the anchoring portion 12, the mounting portion 14, and the stem protuberances 16a, 16b) can be constructed of a rigid material such as metal, alloy, or ceramic. If the rigid material is metal or alloy, appropriate materials can include, for example, titanium, stainless steel, and cobalt chrome.

Turning to FIG. 2, a side view of the stem component 10 is shown. As can be seen, the stem protuberances 16a are configured to span a distance of approximately one half of the depth of the mounting portion. The stem protuberance 16b (not shown) is configured similarly. In FIG. 3, a top view of the stem component 10 is shown. As the mounting portion 14 is configured in a dovetail-type shape, the stem protuberances 16a, 16b are not visible from this perspective, and thus, are shown as dashed lines.

Figure 7:
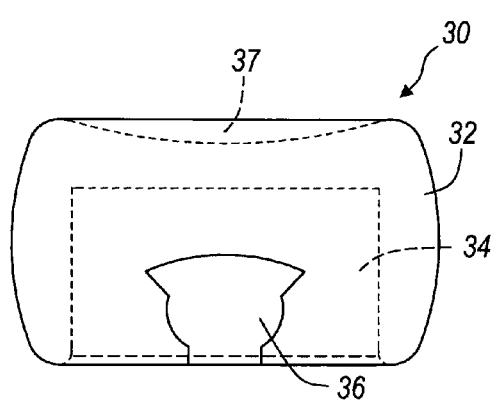
FIG. 7 is a front view of an outer shell of the head component.
Figure 8:
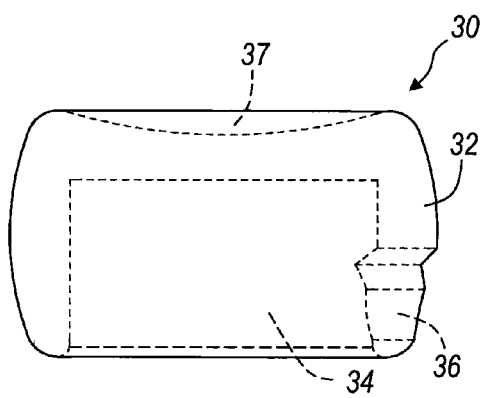
FIG. 8 is a side view of an outer shell of a head component from a perspective perpendicular to that of FIG. 7.

The stem component shown in FIGS. 1-3 has the dual purpose of attaching the prosthesis to the radius bone, as well as to provide a mechanism to mount a head component (not shown) to the stem component. Though the head component can be a single unit, in the embodiment shown in the subsequent figures, the head component comprises an outer shell and an inner core. The practical reason for this is that it is often desirable to have a rigid outer shell, while having a less rigid inner core when utilizing the locking mechanism described in FIGS. 1-13. However, if the locking mechanism does not utilize compressible protuberances as part of the locking mechanism, the inner core can be a rigid material as well. FIGS. 3-6 show an embodiment of the inner core, and FIGS. 7-8 show an embodiment of the outer shell. However, the inner core and the outer shell will generally be pre-assembled prior to surgery.

Turning specifically to FIG. 4, an inner core 20 of a head component is shown. An inner core body 22 defines the shape of the inner core 20 and can be constructed of a polymeric resin, such as, for example, a high molecular weight polyethylene. Additionally, the outer dimension of the inner core body 22 can be cylindrical in shape. Attached to the inner core body are a pair of inner core protuberances 24a, 24b. The inner core body 22 and the inner core protuberances 24a, 24b define an inner core open channel or groove 26 that can be slidably connected to the mounting portion (not shown) of the stem component (not shown). The inner core protuberances 24a, 24b can be constructed of the same material as the inner core body 22, though this is not required. Thus, the inner core body 22 and the inner core protuberances 24a, 24b can be a single polymeric or copolymeric unit. Whatever the structure, in this embodiment, the inner core protuberances 24a, 24b are constructed of a compressible material so that the inner core protuberances 24a, 24b can pass by the stem protuberances (not shown) as part of a locking mechanism.

Figure 5:
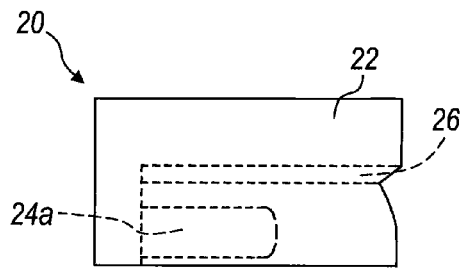
FIG. 5 is a side view of the inner core of the head component from a perspective perpendicular to that of FIG. 4.
Figure 6:
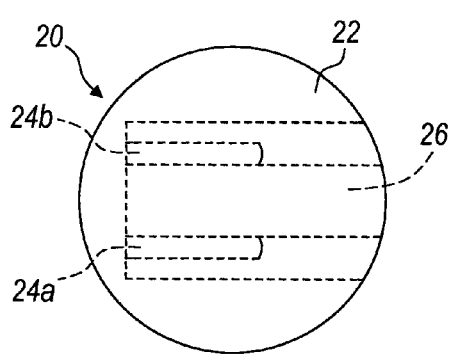
FIG. 6 is a top view of the inner core of the head component.

As can be seen more clearly in FIGS. 5 and 6, the inner core protuberances 24a, 24b are configured such that they span only a portion of the depth of the open channel 26. Thus, the inner core protuberances 24a, 24b are positioned opposite the stem protuberances (not shown) such that when the head component is in place on the stem component, all of the protuberances act together to form a locking mechanism.

As shown in this embodiment, the inner core open channel 26 does not traverse completely through the inner core body 22. Thus, the inner core groove 26 is just long enough such that when the mounting portion of the stem component (not shown) is tracked within the inner core open channel 26, the mounting portion and the inner core 20 will be coaxial.

In FIGS. 7 and 8, a radial head component 30 is shown. An outer shell body 32 is fashioned to approximate the dimensions of a damaged or removed radial head. Thus, the outer dimension is roughly cylindrical, having a slightly concaved top portion 37 for natural articulation with the capitellum (not shown). Because outer shell body 32 is the portion of the prosthesis that will articulate with the capitellum upon joint movement, this structure can be constructed of a biologically acceptable rigid material. Such a material can include, for example, metal, alloy, or ceramic. If the rigid material is metal or alloy, appropriate materials can include, for example, titanium, stainless steel, and cobalt chrome. The outer shell body 32 also defines an inner hollow 34 that accepts the inner core (not shown) when the head component is fully constructed. Additionally, an outer shell open channel or groove 36 is present that essentially matches the inner core open channel or groove (not shown) such that the mounting portion (not shown) can be inserted into the aligned grooves. For example, the outer shell body 32 and the inner core (not shown) can both be cylindrical components that define dovetail shaped grooves, which substantially fits the dovetail shaped mount of the stem component. If the inner core 20 and the outer shell body 32 are two different materials (as in the present embodiment), then the two components can be fitted together with a bonding cement, friction fit, and/or other known techniques. The outer shell open channel or groove 36 can be present at only one edge of the outer shell body 32 and its edges can be tapered to avoid damage to the articular cartilage of the proximal radial-ulnar joint. As mentioned, the outer shell body 32 should be composed of metal suitable for biologic implantation, and be shaped to approximate the dimensions of the radial head. If the surgeon requires assistance in selecting an appropriately sized head component, then an estimate of the patient's anatomy can be ascertained using plastic trials (not shown) provided for this purpose. Though not required, the edges of the outer shell groove 36 can be tapered to avoid damage to the proximal radial-ulnar joint.

Figure 9:
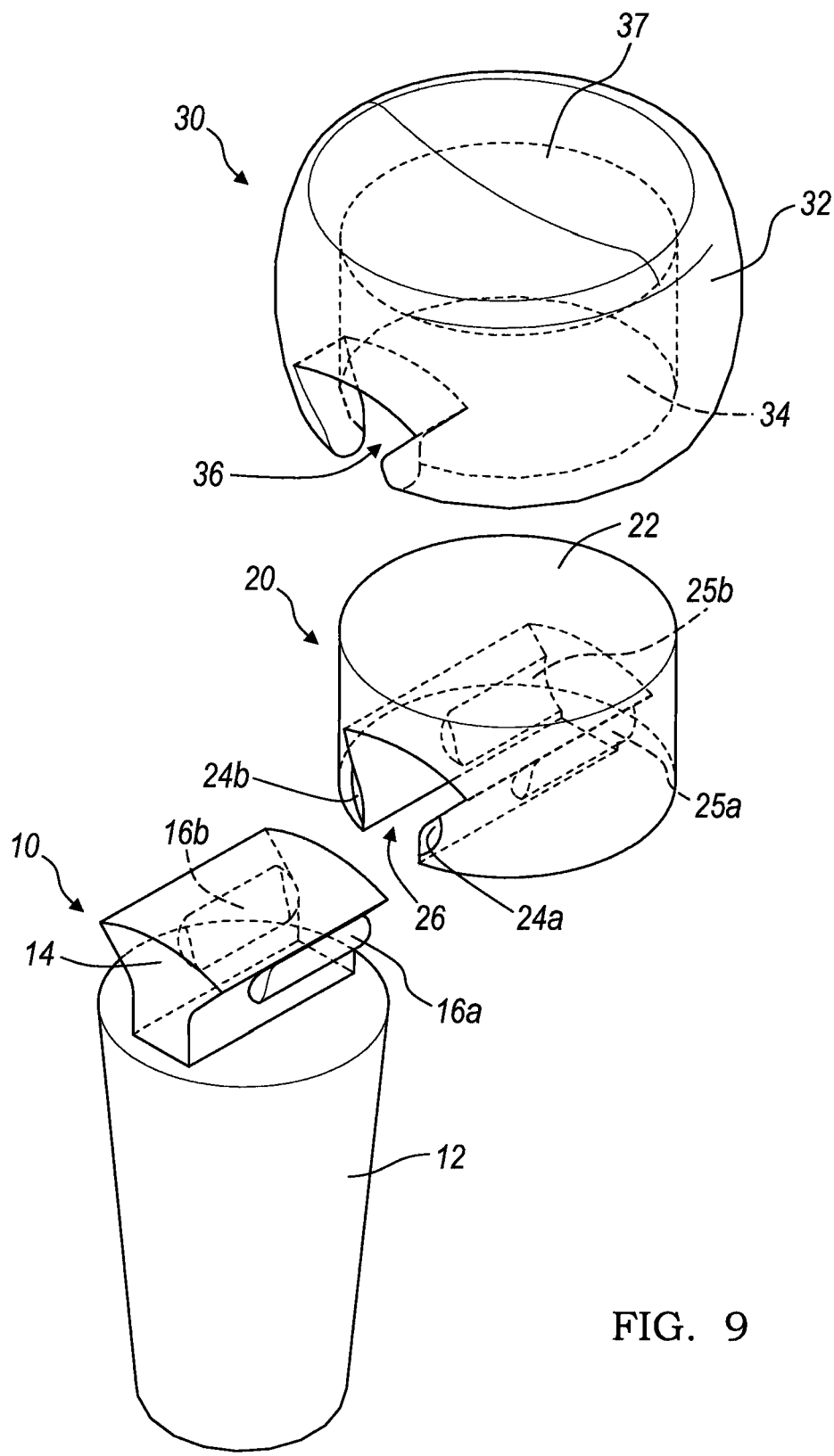
FIG. 9 is an exploded perspective view of an assembly of a stem component, an inner core, and an outer shell.

Turning to FIG. 9, an exploded view of an embodiment of the present disclosure is shown. Specifically, the radial head component 30 is shown having an outer shell body 32, which defines an outer shell hollow 34. The outer shell hollow 34 fits over an outer dimension of the inner core body 22 of the inner core 20. Once the outer shell body 32 and the inner core 20 are fitted together such that the outer shell open channel 36 aligns with the inner core open channel 26, the entire head component (which comprises these two components) can be fitted on the mounting portion 14 of the stem component 10. Though not required, the locking mechanism can be at an interface between the mounting portion 14 and the inner core 20. As shown in this figure, a pair of the stem protuberances 16a, 16b can pass over a pair of the inner core protuberances 24a, 24b, as the inner core protuberances 24a, 24b are configured to compress. Once the stem protuberances 16a, 16b completely pass over the inner core protuberances 24a, 24b, the stem protuberances can lock into a pair of inner core concavities 25a, 25b, respectively. The inner core concavities 25a, 25b are configured in dimension to inversely match the stem protuberances 16a, 16b such that a locking action occurs. Thus, an abutment of the protuberances occurs and can prevent unwanted motion between the head component and the stem component after the prosthesis is inserted. The protuberances also serve to prevent the head component from slipping off the stem component without intentional force, e.g., during removal by a surgeon. With this and other similar designs, the stem component can be placed in a canal of the radius bone, followed by the fitting of the head component.

Figure 10:
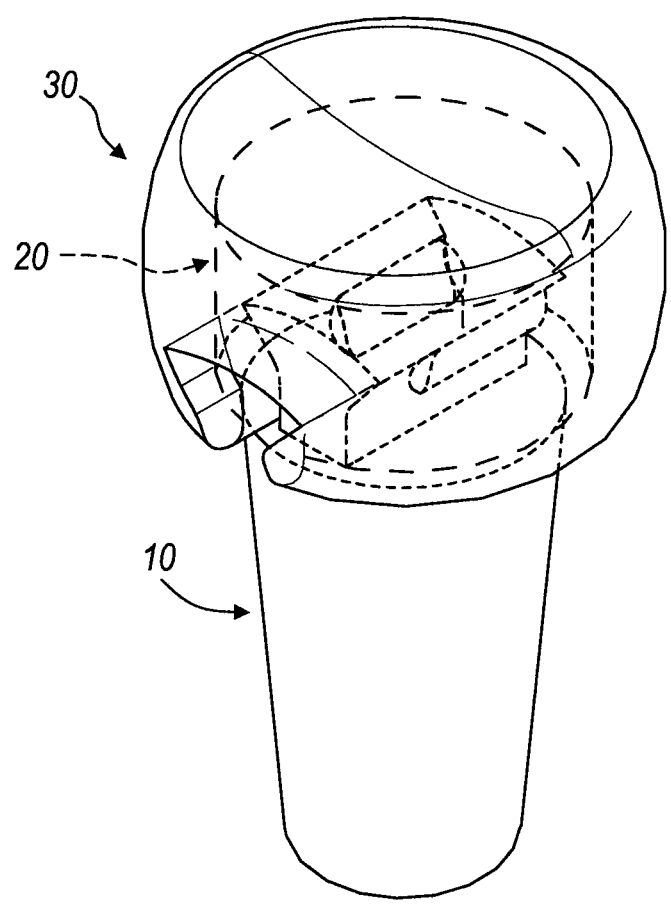
FIG. 10 is a perspective view of an assembled prosthesis.

FIG. 10 shows the stem component, the inner core 20 and the outer shell body 32 in a completed assembly configuration. As can be seen, the cylindrical inner core 20 component fits centrally within the outer shell body 32. Thus, when the mounting portion 14 of the stem component 10 is inserted fully within the core and shell, all three components will be configured coaxially. Though the outer shell body 32 and the inner core 20 are shown as two separate components, in practice, the outer shell body 32 and the inner core 20 can be assembled and sterilized prior to attachment to the mounting portion 14 of the stem component 10. Thus, the surgeon would only be required to slide the assembled head component onto the stem component 10 by lining up the open channels 26, 36 with the mounting portion 14, and sliding the radial head component 30 into place. In FIGS. 11-13, additional views of an assembled prosthesis are shown.

When assembling the head component onto the mounting portion 14, due to elastic deformation of the inner core protuberances 24a, 24b, all of the protuberances 16a, 16b, 24a, 24b can be slid past opposing protuberances under sufficient translational force. In this embodiment, the protuberances are shaped such that the force required to press the protuberances past their opposing protuberances is intentional and reasonable, but not excessive.

Figure 14:
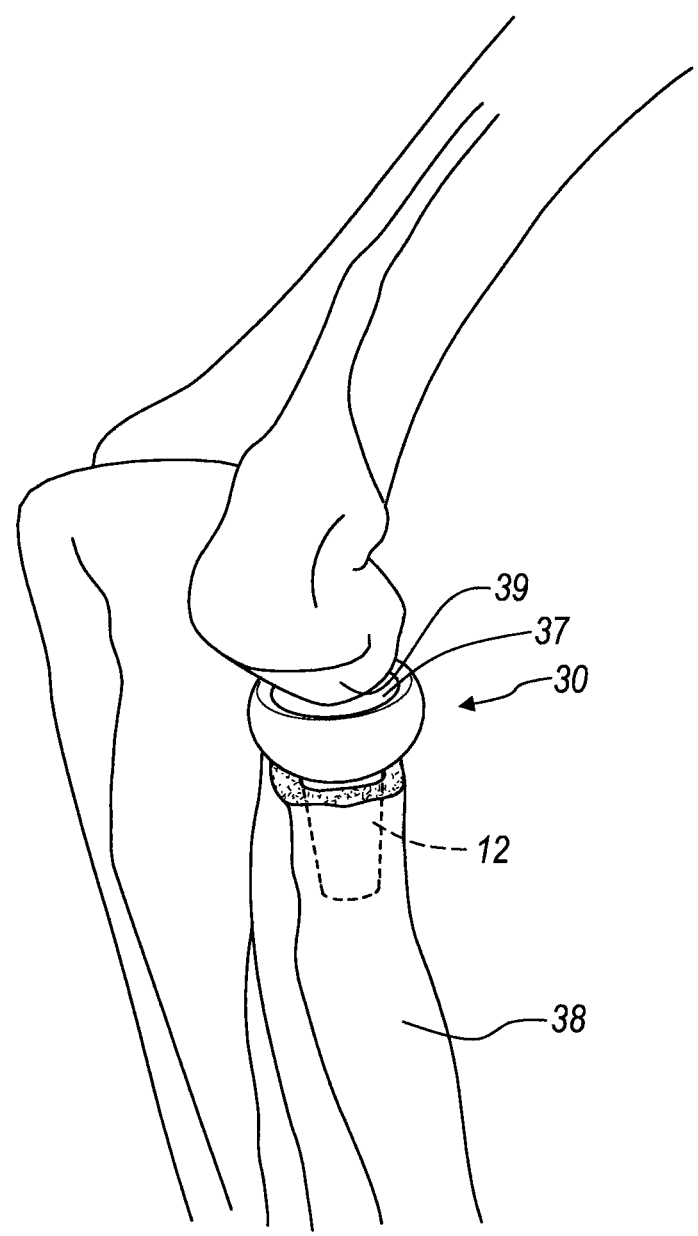
FIG. 14 is a posterior oblique view of a human elbow depicting a radial head prosthesis in position within a proximal radius bone and articulating with a capitellum of a distal humerus.

FIG. 14 is a posterior oblique view of the human elbow depicting the radial head prosthesis in position within the proximal radius bone 38 and articulating with the capitellum 39 of the distal humerus. As can be seen, the anchoring portion 12 is within the medullary canal of the proximal radius 38, and the radial head 30 is articulating with the capitellum 39 of the distal humerus.

Figure 15:
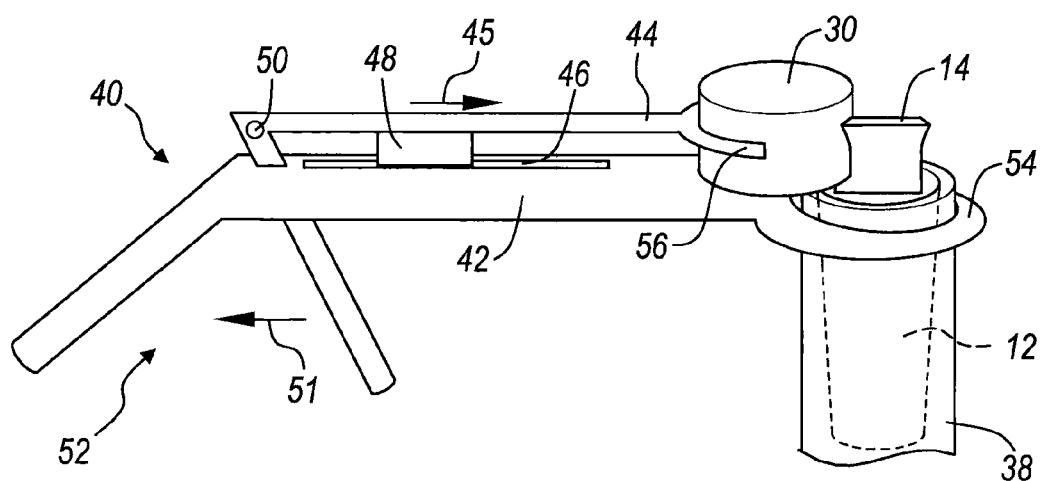
FIGS. 15 and 16 are perspective views of a tool that can be used to insert or remove a head component from a stem component via a translational force.
Figure 16:
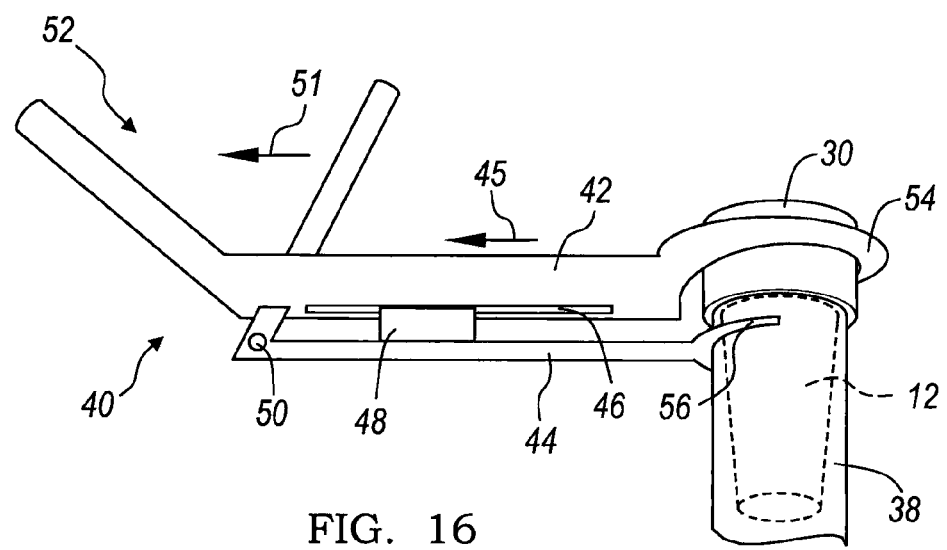

In FIGS. 15 and 16, a tool 40 is shown that can be used with the prosthesis of the present disclosure is shown. In FIG. 15, the tool 40 is positioned in a first orientation with respect to proximal radius 38 for inserting the radial head component 30 onto the mounting portion 14. In FIG. 15, the tool 40 is positioned in a second orientation with respect to the proximal radius 38 for removing the radial head component 30 from the mounting portion.

Specifically, with respect to FIG. 15, a first arm 42 and a second arm 44 are shown that enable a surgeon to create translational force 45 to be placed on the radial head component 30. The first arm 42 and the second arm 44 are tracked parallel to one another by a track 46 and a slider 48. The second arm 44 is connected to a handle 52 by a hinge 50. The handle 52 is designed such that by applying a squeezing force 51, translational force 45 is applied to the head component 30. Thus, in this embodiment, the translational force mechanism is a lever. At the end of the first arm 42 is a pulling member 54 that acts to stabilize the proximal radius 38 (or alternatively, the mounting portion 14). At the end of the second arm 44 is a pushing member 56 for pushing the radial head component 30 onto the mounting portion 14.

In FIG. 16, the same tool 40 as described in FIG. 15 can be used by flipping it upside down. Thus, the first arm 42 now acts to provide the translational force 45 and the second arm 44 stabilizes the proximal radius 38 (or alternatively, the mounting portion 14). Thus, the arms are characterized as the first arm 42 and the second arm 44 for convenience only. It would be apparent to one skilled in the art that the first arm or the second arm can function as the stabilizer. Likewise, the first arm or the second arm can act to provide desired translational force.

The use of such a tool is particularly helpful when a locking mechanism such as that described in FIGS. 1-13 is in place. Locking and unlocking can be carried out as previously described. Specifically, in the present embodiment, the tool can press the components onto one another while maintaining alignment of the dovetail shaped mount and groove. In the absence of intentional and sufficient pressure to translate the head component off of the stem component, the rigidity provided by the polyethylene is sufficient to secure the modular components to each other. Removal is accomplished by generating sufficient translational pressure on the head component with the use of a specially designed handle. This tool binds the far end of the head component while stabilizing the proximal radius bone, and thereby the stem component. Translational force is generated which presses the protuberances of the inner core past the protuberances of the mounting portion, thereby releasing the head component from the stem component.

A procedure that can be followed for the insertion of the modular radial head prosthesis is as follows. If necessary, after resection of a substantially unreconstructable radial head bone, a proximal edge of the radius bone can be removed by transverse sawing or some other removal technique. After the damaged radial head has been removed, the medullary canal of the bone can then be broached with one or more of a series of broaches, the shapes of which approximate the various stem sizes available. Once an appropriate size stem component size has been selected, the anchoring portion can be inserted into the proximal radius bone such that the mounting portion protrudes from the proximal radius bone. The head component can then be selected based upon parameters such as proper ligament tensioning, circumference, and height. If desired, this assessment can be assisted with the use of plastic trials made available for this purpose. After an appropriately sized head component is selected, the forearm can be rotated so that the mounting portion is positioned to receive the head portion, i.e., an assembled outer shell/inner core combination or a single piece head component. If the head component comprises an outer shell and an inner core, the head component can either be assembled at the time of manufacture or by the surgeon. In any event, the outer shell groove and the inner core groove should be positioned such that the grooves line up for accepting the mounting portion. Once the stem component is in place and the proper head component is assembled and selected, the head component is then translated onto the stem component fully. If a locking mechanism is used such as that described in FIGS. 1-13, a click will be palpable as the stem protuberances and the inner core protuberances slip fully past each other. The prosthesis will then be secure within the canal of the proximal radius bone and is positioned to articulate with the capitellum of the distal humerus.

With the above figures and surgical procedures in mind, a modular prosthesis system for replacement of the radial head portion of the radius bone is disclosed comprising a stem component and a head component. The stem component comprises an anchoring portion and a mounting portion, and the head component can have an open channel configured to connect to the mounting portion along an assembly axis that is transverse to a longitudinal axis of the stem component. The connection can be by a sliding motion. Though the system requires only that the assembly axis be transverse to the longitudinal axis of the stem component, for practical purposes, the transverse angle will generally be from about 45° to 135° with respect to the longitudinal axis. This is due to the fact that as you approach angles closer to parallel with the longitudinal axis, the head component becomes more difficult to put in place. In many incidences, the assembly axis will intersect the longitudinal axis at essentially a perpendicular angle.

The system can further comprise a locking mechanism to prevent the open channel of the head component from indeliberately sliding on the mounting portion once connected to the mounting portion. This is desirable because once the prosthesis has become part of the functioning elbow joint, any slippage could require surgery for repair. Thus, the only circumstance wherein sliding should be allowed should occur at the hand of the surgeon, with deliberate action. The locking mechanism can be configured such as that shown in FIGS. 1-13, or by any other locking mechanism known by those skilled in the mechanical arts. For example, after sliding the head component onto the mounting portion, the head component can be locked in place with a pin or screw.

In one embodiment, the mounting portion can be configured for allowing the head component to slide along a single axis via the open channel. Such an embodiment is shown in FIGS. 1-13 where the dovetail-shaped mounting portion is inversely matched with a dovetailed-shaped groove. Thus, the head component can be slid onto the mounting portion along a single axis only.

Though not required, the head component can be inserted and removed from the mounting portion with a specially designed tool. Thus, the system of the present disclosure can further comprise a tool for inserting and removing the head component while the stem component is in place within a radial canal. Such a tool can comprise a first arm for inserting the head component onto the mounting portion or removing the head component from the mounting portion; a second arm for stabilizing the radius bone; and a translational force mechanism for moving the first arm while the second arm stabilizes the radius bone. The terms "translation" and "stabilizing" are used loosely depending on whether the tool is being used for insertion or removal of the head component, the arm acting to provide the translational force and the arm acting to provide stabilization can be changed. Thus, the terms are relative as to the action, rather than to the specific structure. For example, when insertion of the head component is being carried out, the first arm carrying out the translational insertion does so by a pushing force, and the second arm stabilizes the radius bone by a pulling force. Conversely, when removal of the head component is being carried out, the first arm removes the head component by a pulling force (i.e., the tool is flipped over, and the second arm stabilizes the radius bone by a pushing force).

As part of the system, a method for fitting a damaged radius bone with a modular radial head prosthesis is disclosed comprising the steps of securing a stem component partially within a proximal intramedullary canal of the damaged radius bone such that a mounting portion of stem component is exposed above the damaged radius bone; selecting a head component that will provide a desired result; and sliding the head component onto the mounting portion in a direction along an assembly axis that is transverse to a longitudinal axis of the stem component. Typically, a preliminary step of removing a radial head of the damaged radius bone is carried out prior to fitting the radius bone with the prosthesis of the present disclosure, though there can be circumstances where this preliminary step is not necessary. Additionally, before securing the stem component within the intramedullary canal, it may be desirable to carry out the preliminary step of sizing the stem component to securely fit within the proximal canal. This can be done using a set of broaches designed for this purpose. The stem component can be secured within the intramedullary canal by one of a number of techniques including the use of cement, firm pressure into the canal, or impacting the stem component into the canal, for example.

Once the stem component is in place, the next step of selecting an appropriate head component is carried out. Considerations can include assessing a desired tensioning of one or more ligaments attached to the radius bone and/or assessing the height and shape of the head component to be used. Aid in this area can be provided by the use of trials designed for this purpose. Such trials can be plastic structures configured to approximate the size and shape of the head component to be ultimately placed on the mounting portion. It is appreciated that the trials can be made of other suitable materials.

Referring to FIGS. 17 through 20, the inner core 20 and the outer shell body 32 of the radial head component 30 are shown. In the various embodiments, the outer shell body 32 can be comprised of ultra high molecular weight polyethylene (UHMWPE). The outer shell body 32 can also be comprised of a suitable metal material such as cobalt chrome, titanium, or other biocompatible material. The inner core 20 can also be made of a material that is identical to the radial head component 30 (FIG. 19B) or as above described made of a softer material (FIG. 19A) that can otherwise be compressed when inserted over the stem protuberances 16a, 16b or any other biocompatible material, as above detailed and as shown in FIG. 1.

Figure 17:
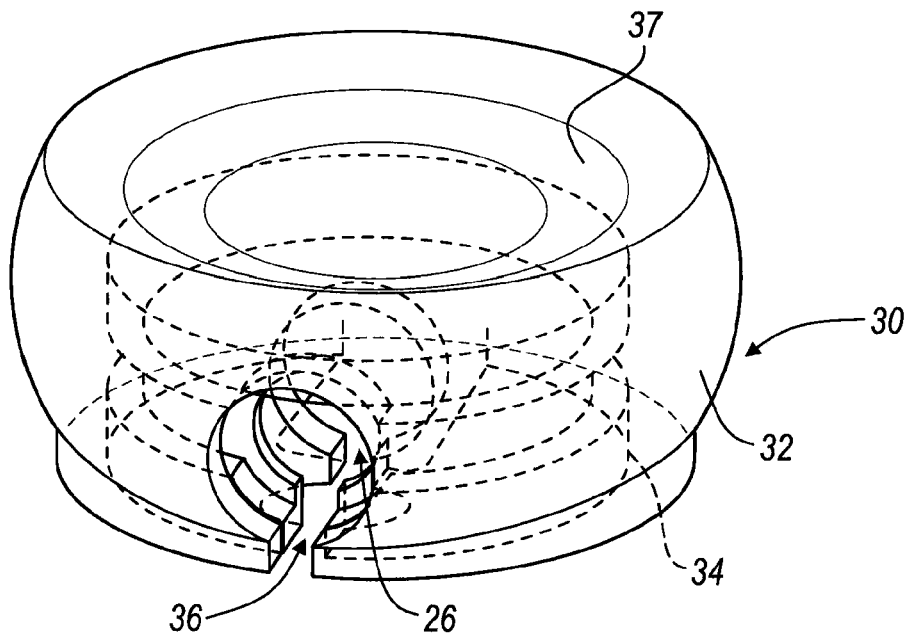
FIG. 17 is a perspective view of the head component showing the outer shell body completely enveloping the inner core.
Figure 18:
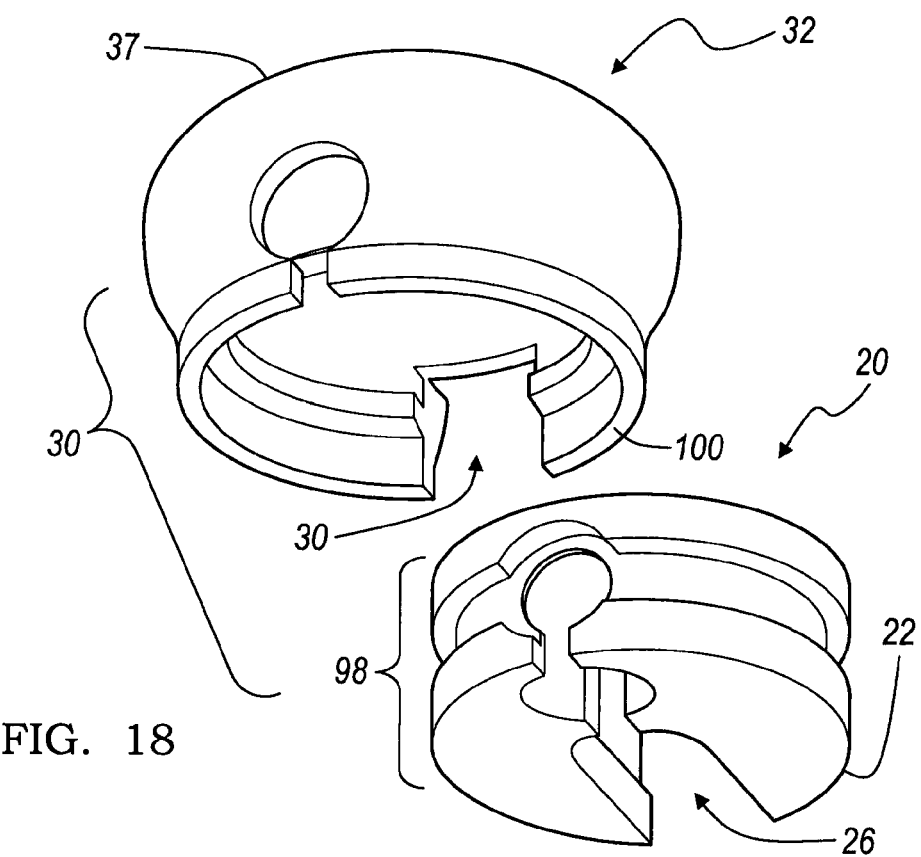
FIG. 18 is similar to FIG. 17 but shows the head component disassembled.
Figure 19A:
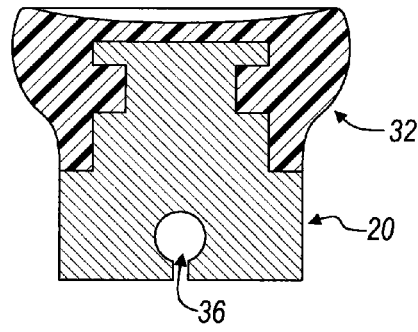
FIG. 19A is a perspective view of the head component showing the inner core extending beneath the outer shell body.
Figure 19B:
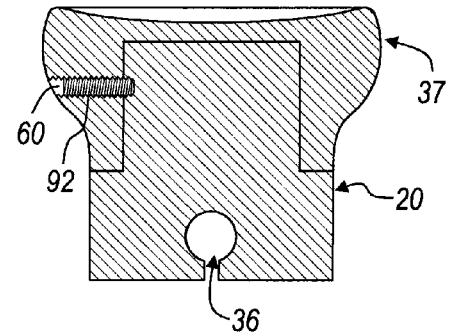
FIG. 19B is similar to FIG. 19A but shows a mechanical fastener securing the outer shell body to the inner core.
Figure 19C:
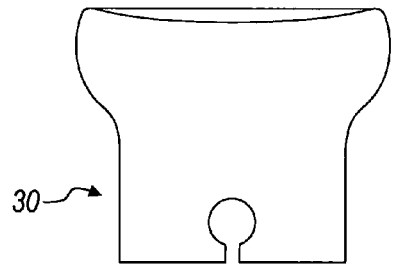
FIG. 19C is similar to FIG. 19A but shows the head components as a single piece.
Figure 20:
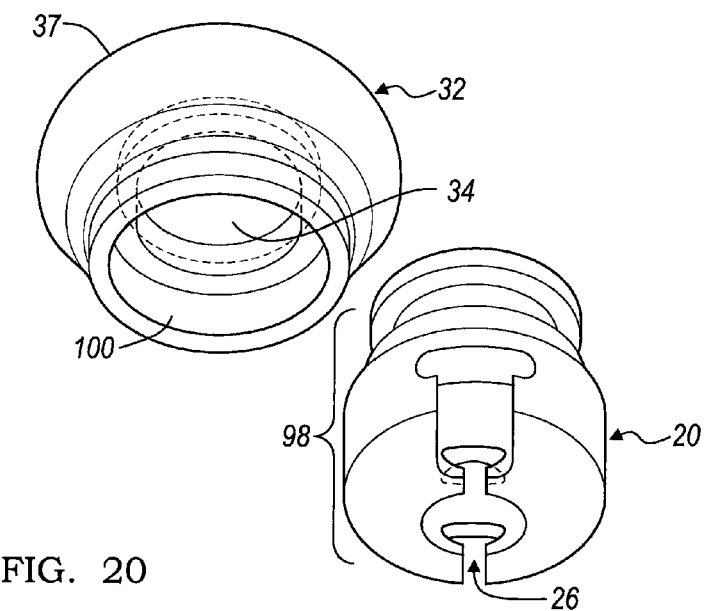
FIG. 20 is similar to FIG. 19 but shows the head component disassembled.

In other embodiments, the inner core 20 and the outer shell body 32 are comprised of the same material (FIG. 19B), for example, a metal such as cobalt chrome or titanium. By way of example, a mechanical fastener 60 can be used to secure the outer shell body 32 to the inner core 20 in lieu of the compressible inner core protuberances 24a, 24b (FIG. 4). In addition, the head component 30 can be made of single piece of biocompatible material (FIG. 19C), such that the head component is a unitary construction. It is appreciated that a plurality of the fasteners 60 can be used to secure the outer shell body 32 to the inner core 20. Moreover, other types of exemplary connections may be used such as chemical bonding, shrink fit and taper junctions. Furthermore, the outer shell body 32 can be configured to snap fit onto the inner core 20, while another method can include mechanical threading on the inner core 20 with complementary mechanical threading on the outer shell body 32. The outer body shell 32 of the radial head component 30 can also be configured to completely envelope the inner core 20, as shown in FIGS. 17 and 18, or otherwise be positioned over the inner core 20 as to not cover the open channel 26 thus exposing varying lengths of the inner core 20, as shown in FIGS. 19A, 19B and 20.

Figure 21A:
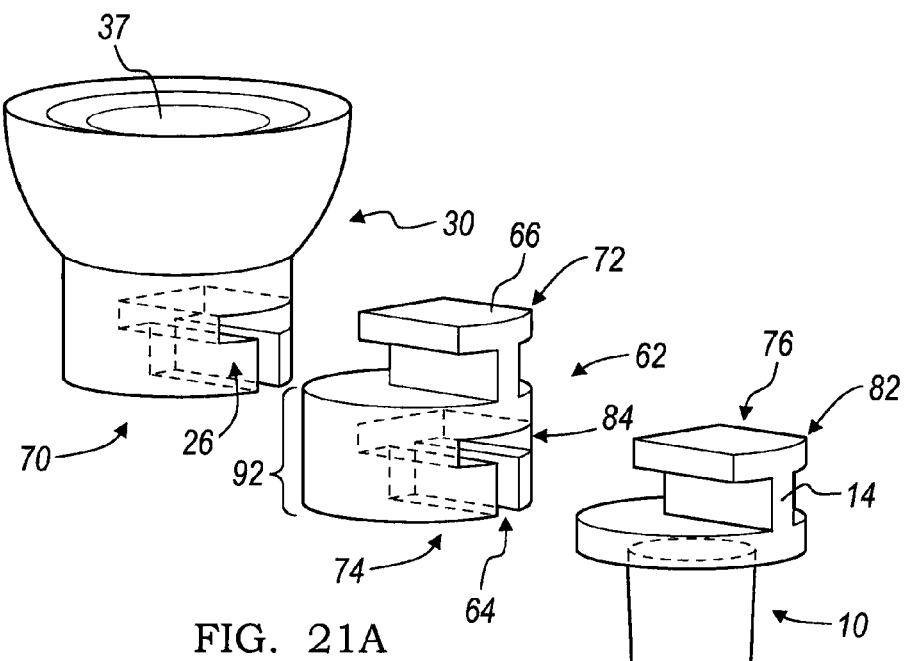
FIG. 21A is a perspective view of the head component, the stem component and a collar component.
Figure 22:
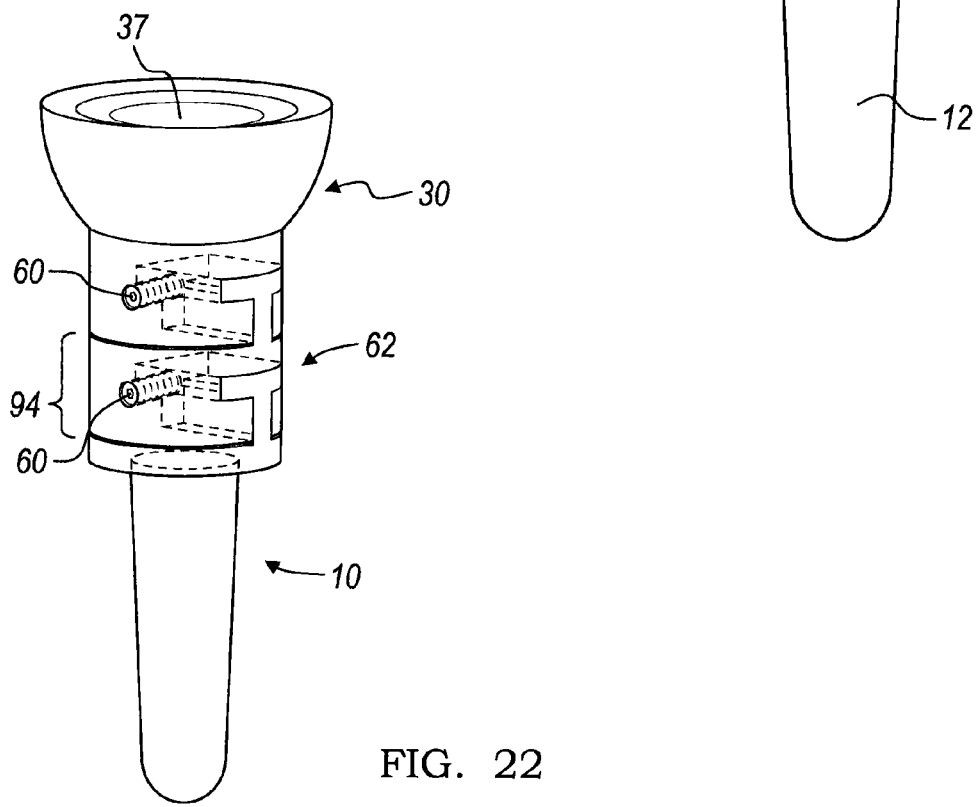
FIG. 22 is similar to FIG. 21A but the components are assembled.
Figure 25:
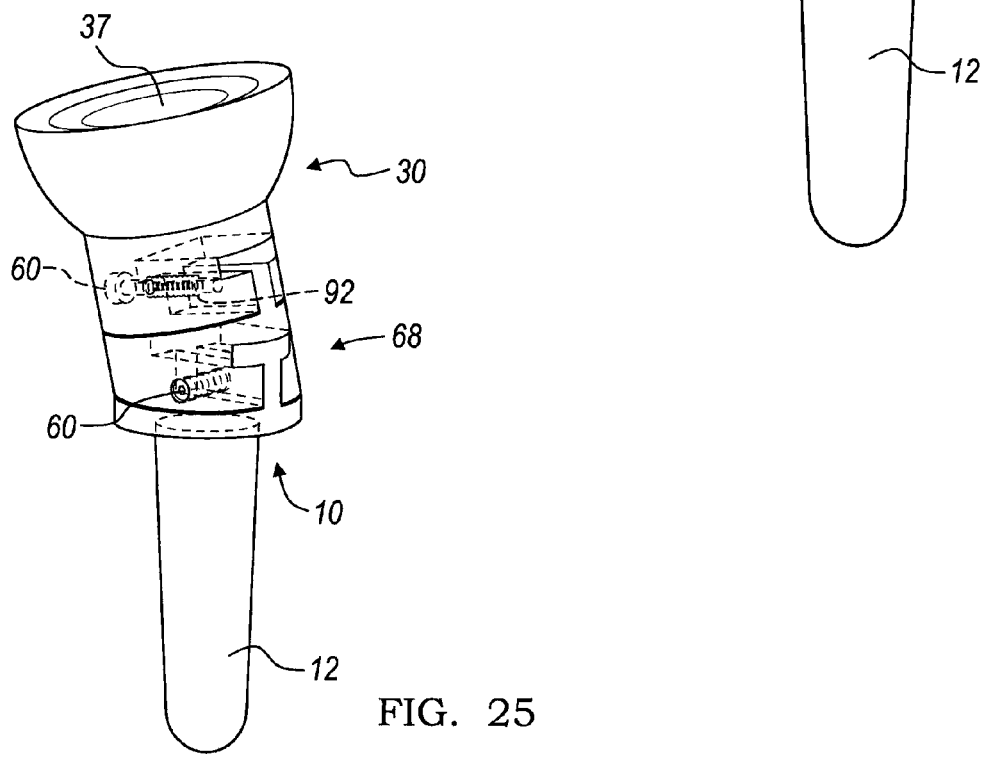
FIG. 25 is similar to FIG. 24 but the components are assembled.

With reference to FIGS. 21A through 24, a collar component 62 can be used to connect the radial head component 30 to the stem component 10. The collar component 62 can have a collar open channel 64 and a collar mounting location 66, which are complementary to the head open channel 36 and the stem mounting location 14, respectively. The collar component 62 can be configured to vertically align the radial head component 30 and the stem component 10, as shown in FIG. 22. An angled collar component 68 can also be configured to provide a pre-determined angle between the radial head component 30 and the stem component 10, as shown in FIG. 25. As such, the angled collar component 68 can be configured at various angles, for example, between vertical (i.e., 180°) and narrower angles to match the native geometry of the bones, as shown in FIG. 14. It can be appreciated that the radial head component 30 and the stem component 10 can attach to the collar component 62 or the angled collar component 68 regardless of its length or angle.

In the various embodiments, the radial head component 30 can have a unitary construction (i.e., one-piece), thus omitting the inner core 20 and outer shell body 32. In this arrangement, the radial head component 30 can be constructed of metal such as cobalt chrome, titanium or any other suitable biocompatible material for implementation into the human body. By way of example, the radial head component 30 can be secured to either the stem mounting portion 14 or the collar mounting portion 66 of the collar component 62 with a suitable mechanical fastener 60.

Figure 21B:
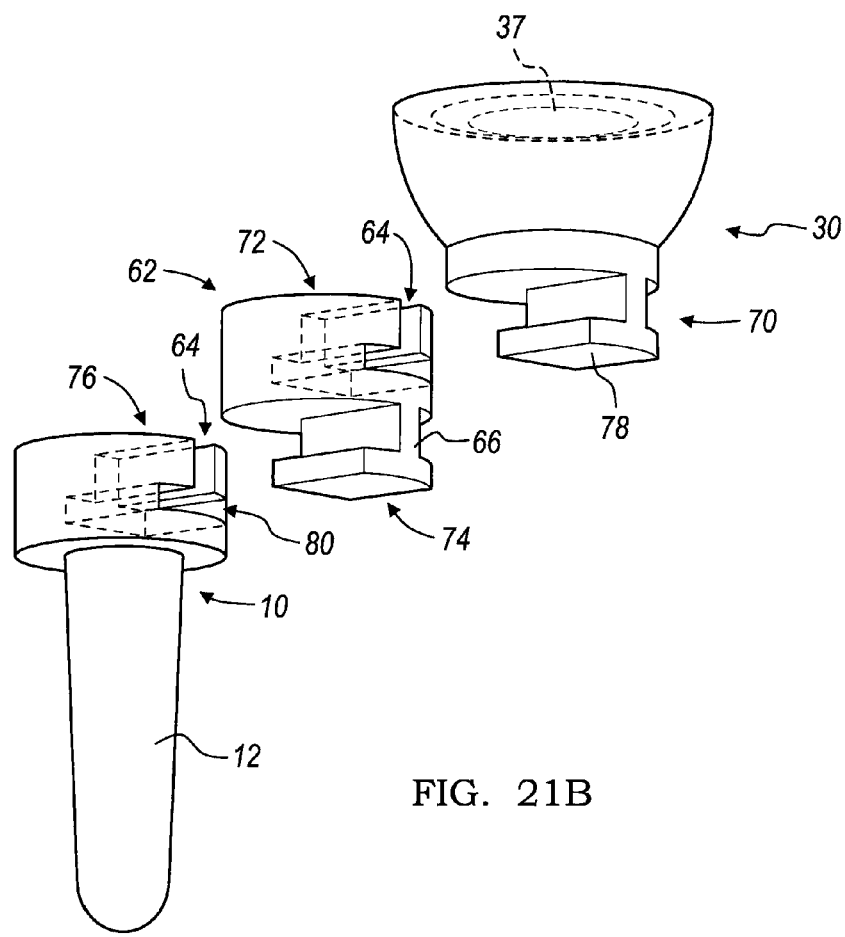
FIG. 21B is similar to FIG. 21A but shows an alternative configuration between the head component, the stem component and the collar component.

With reference to FIGS. 21A and 21B, the head component 30 includes a first connection portion 70 that connects to a second connection portion 72 on the collar component 62. The collar component 62 also includes a third connection portion 74 that connects to a fourth connection portion 76 on the stem component 10. It can be appreciated that the second connection portion 72 can be distal from the third connection portion 74 and can be on opposite ends of the collar component 62. As shown in FIG. 21A, the first connection portion 70 can be the open channel 26 on the head component 30. The second connection portion can be the collar mounting portion 66. The third connection portion 74 can be the collar open channel 64. The fourth connection portion 76 can be the mounting portion 14 on the stem component 10. As shown in FIG. 21B, the first connection portion 70 can be a head component mounting portion 78. The second connection portion can be the collar open channel 64. The third connection portion 74 can be the collar mounting portion 66. The fourth connection portion 76 can be a stem component open channel 80.

Figure 23:
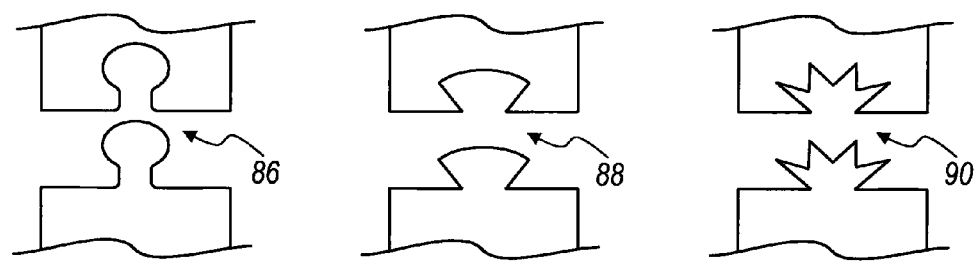
FIG. 23 are perspective views of exemplary alternative connections between components of the modular prosthesis.
Figure 24:
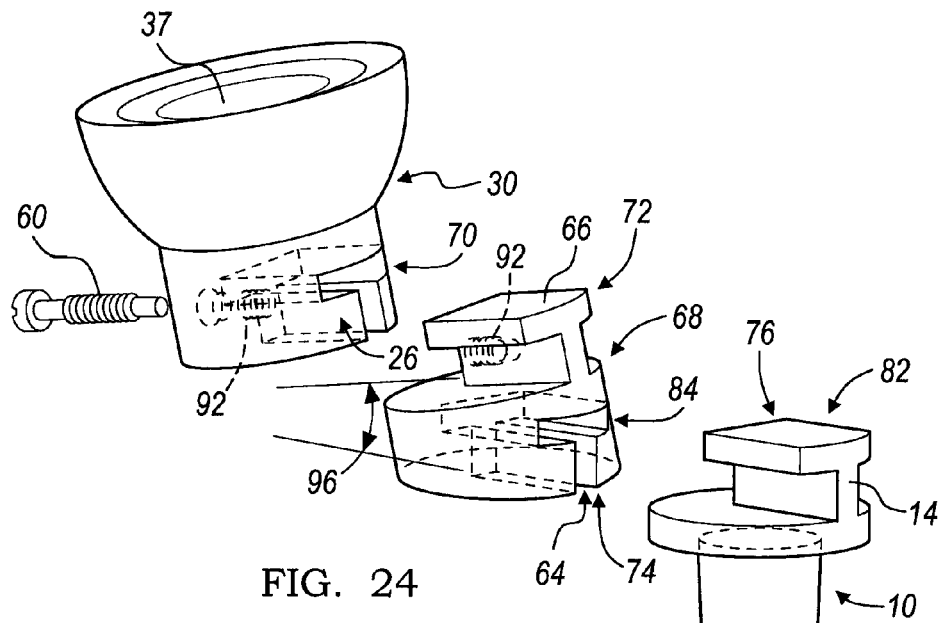
FIG. 24 is similar to FIG. 21A but shows an angled collar component.

It can be appreciated that the various components of the modular prosthesis system can use various connection portions with myriad configurations. By way of example, the mounting portion on the various components is configured in a T-shaped protrusion generally indicated by reference numeral 82. A complementary open channel 84 is similarly configured in a T-shape to accept the T-shaped protrusion 82. With reference to FIG. 23, it can be appreciated that other configurations are suitable such as, but not limited to, a cylindrical configuration 86, a dove-tail configuration 88, and a star shaped configuration 90. It can also be appreciated that, regardless of the configuration, various fits can be used such as, but not limited to, an interference fit, a taper lock fit and a sliding fit secured by a mechanical fastener 60. It can further be appreciated that the mechanical fastener 60 can be inserted through an aperture and contact the T-shaped protrusion. The mechanical fastener can also connect to the T-shaped protrusion such that the fastener 60 can be inserted through a fastener aperture 92 in the open channel and/or in the mounting location. It can be additionally appreciated that the fastener can be placed at various angles and positioned to further secure the components of the prosthesis.

It can be appreciated that the various components of the modular prosthesis can be scaled to fit the patients native bone structure. A collar length 94 (FIG. 22) and a collar angle 96 (FIG. 24) can be variable among multiple collar components 62, 68, while the collar mounting location 66 and the collar open channel 64 can have a fixed dimension to facilitate interchangeability among other stem components 10 and head components 30. With reference to FIG. 20, it can also be appreciated that an inner core length 98 can vary such that the inner core body 22 can be completely contained within the head component inner hollow 34 or extend beyond an outer body shell aperture 100. It is further appreciated, that various dimensions such as length, diameter, thickness etc. can be varied to more closely match the native bone structure of the patient, as shown in FIG. 14.

Figure 26A:
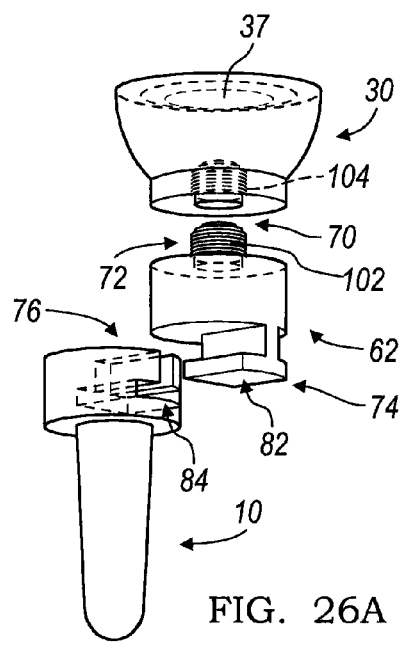
FIGS. 26A-26D are perspective views of exemplary alternative connections between the head component, the stem component and the collar component.

With reference to FIGS. 26A-26D, a threaded post 102 and a complementary threaded aperture 104 can be used to connect the collar component 62 to the head component 30 and the stem component 10. With reference to FIG. 26A, the first connection portion 70 of the head component 30 can include the threaded aperture 104. The second connection portion 72 of the collar component 62 can include the threaded post 102 that can engage with and connect to the complementary threaded aperture 104 on the head component 30. The third connection portion 74 of the collar component 62 can include the above described T-shaped protrusion 82. The fourth connection portion 76 of the stem component 10 can include the above described T-shaped channel 84, which can connect with the T-shaped protrusion 82 included on the third connection portion 74 of the collar component 62. It can be appreciated that the angled collar component 68 (FIG. 26D) can be similarly configured to the collar component 62 (FIGS. 26A-26C) and, thus, can be used interchangeably.

Figure 26B:
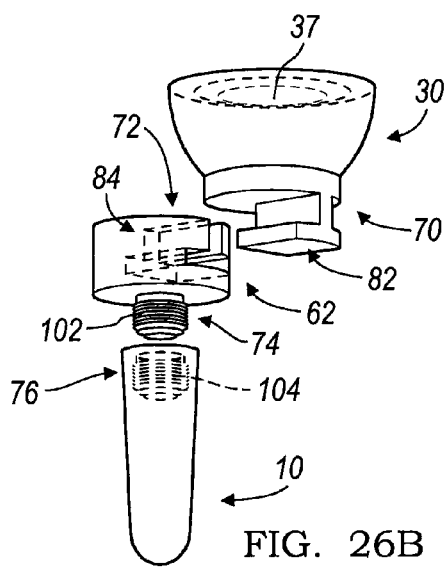

With reference to FIG. 26B, the first connection portion 70 on the head component 30 can include the T-shaped protrusion 82. The second connection portion 72 of the collar component 62 can include the complementary T-shaped channel 84 that can connect with and engage the T-shaped protrusion 82 included on the first connection portion 70 of the head component 30. The third connection portion 74 of the collar component 62 can include the threaded post 102. The fourth connection portion 76 of the stem component 10 can include the complementary threaded aperture 104 that can engage to and connect with the threaded post 102 included on the third connection portion 74 of the collar component 62.

Figure 26C:
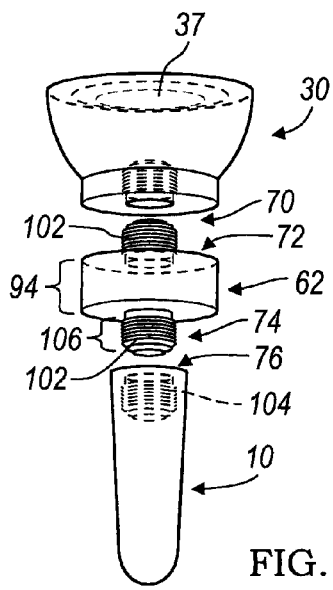

With reference to FIG. 26C, the first connection portion 70 of the head component 30 can include the threaded aperture 104. The second connection portion 72 of the collar component 62 can include the threaded post 102 which can engage with and connect to the threaded aperture 104 included on the first connection portion of the head component 30. The third connection portion 74 of the collar component 62 can also include the threaded post 102. The fourth connection portion 76 on the stem component 10 can include the threaded aperture 104 that can engage with and connect to the threaded post 102 on the third connection portion 74 of the collar component 62.

Figure 26D:
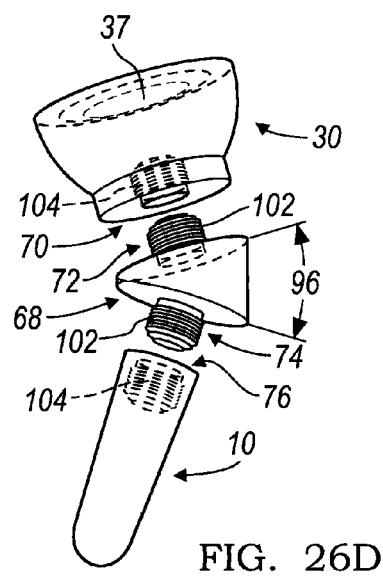

With reference to FIG. 26D, the first connection portion 70 of the head component 30 can include the threaded aperture 104. The second connection portion 72 of the angled collar 68 can include the threaded post 102, which can engage with and connect to the threaded aperture 104. The third connection portion of the angled collar 68 can also include the threaded post 102. The fourth connection portion 76 of the stem component 10 can include the threaded aperture 104, which can engage with and connect to the threaded post 102. It can be appreciated that height 94 (FIG. 26C) and/or angle 96 of either the collar component 62 or angled collar component 68 can be varied to accommodate the native bone structure, as shown in FIG. 14. Moreover, the height 106 (FIG. 26C) of the threaded post 102 can be varied to further accommodate the modularity of the prosthesis. It can also be appreciated that the first connection portion 70, the second connection portion 72, the third connection portion 74 and the fourth connection portion 76 can be configured in various ways including, but not limited to, the respective threaded posts 102 and threaded apertures 104 and various combinations thereof.

Figure 27:
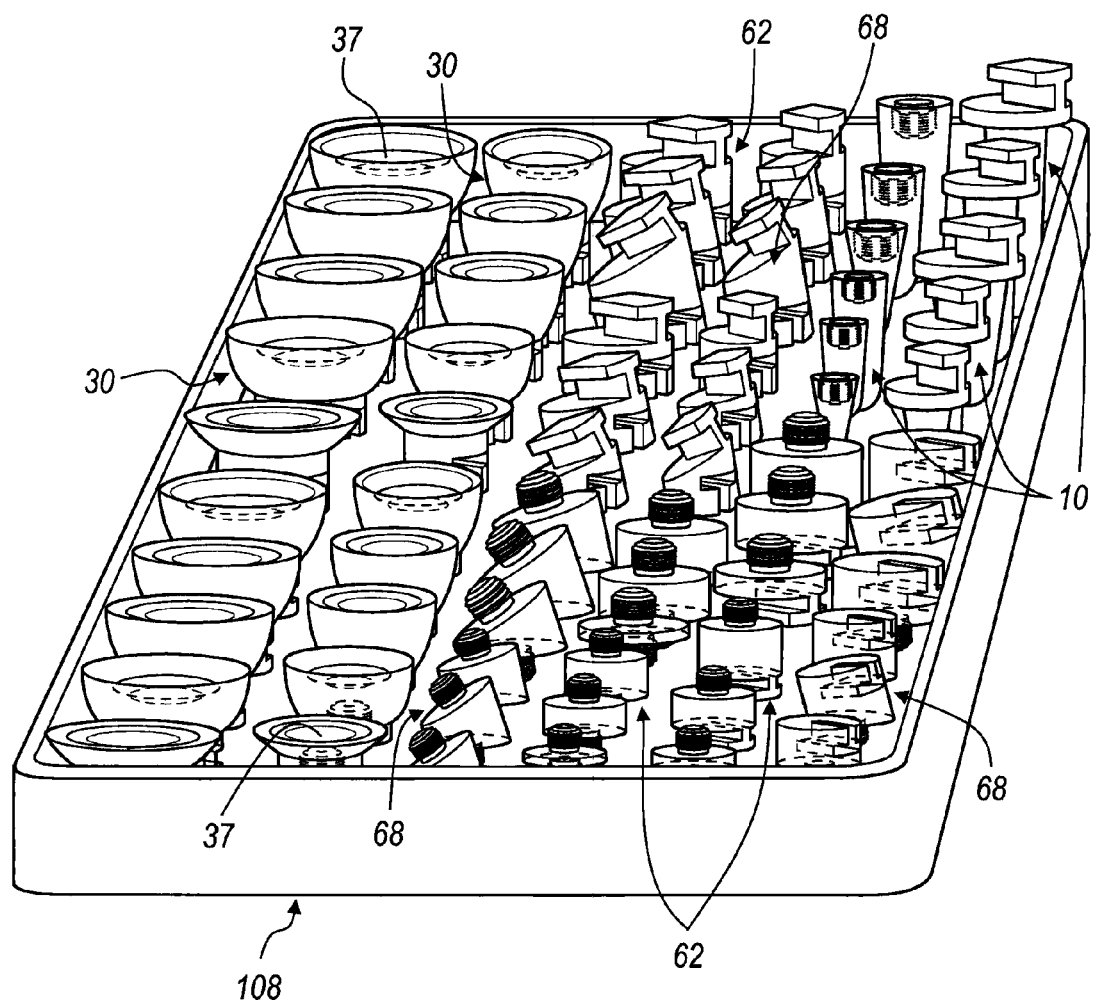
FIG. 27 is a perspective view of a kit including a plurality of head components, stem components and collar components having various sizes, shapes and configurations.

With reference to FIG. 27, a kit 108 is shown including exemplary stem components 10, collar components 62, angled collar components 68 and head components 30. The kit 108 can include a collection of various sizes and shapes of the above-mentioned components. For example, the kit 108 can include a plurality of angled collar component 68 having varying collar angles 96. By way of further example, the kit 108 can include a plurality of head components 30 having varying shaped concave top portions 37 that complement the native bone to which they will contact. The kit 108 can also include a plurality of stem components 10 such that each of the stem components 10 has varying size anchor portions 12 in thickness, taper design and/or length. Moreover, the kit 108 can include a plurality of collar components 62 having varying collar lengths 94 to further accommodate the native bone structure. It can be appreciated that the kit 108 can include numerous head components 30, angled collar components 68, collar components 62, and stem components 10 of various sizes, shapes and configurations so that the modular prosthesis system can be assembled to closely match the native bone structure.

The kit 108 provides the plurality of head components 30, angled collar components 68, collar components 62, and stem components 10 that can be assembled and adjusted during a medical procedure to provide a fit that can be in-situ determined and adjusted. It can be appreciated that a medical professional can determine a proper length and angle and select among the components of the kit 108 to achieve the proper length and angle. Nevertheless, the medical professional can select and substitute components in-situ to adjust to achieve the proper length and angle.

Turning now to FIGS. 28-34, a modular radial head prosthesis system is shown and generally identified at reference numeral 120. The modular radial head prosthesis system 120 can generally include an articulating component 122, a series of head components 124*a*, 124*b* and 124*c* (FIG. 31), a stem component 126 and a fastener 128. As will become appreciated from the following discussion, the modular radial head prosthesis system 120 can provide a series of head components 124*a*, 124*b* and 124*c* having different dimensions (such as height dimensions $H_1$, $H_2$ and $H_3$ (FIG. 31) that can be selectively and alternatively coupled with the articulating component 122, the stem component 126 and the fastener 128. The modular radial head prosthesis system 120 allows a surgeon to use a selected articulating component 122 and choose a desired head component from the plurality or kit of head components according to a patient's particular needs. A common stem component 126 can also be used to selectively interconnect with any of the head components 124*a*, 124*b* and 124*c*. As can be appreciated, different head components having different geometries and/or dimensions may be preferred from one patient to the next. For example, in some cases it may be desired to build up the height (see $H_1$, $H_2$ and $H_3$, FIG. 31) of the distal radius depending upon the amount of host radius that is being replaced. The modularity of the modular radial head prosthesis system 120 can allow a surgeon to have common articulating components 122, stem components 126 and/or fasteners 128 that can be intraoperatively coupled with various head components 124*a*, 124*b* and 124*c* to create an assembled modular radial head prosthesis that provides the desired geometry and profile for any particular patient. It is also appreciated that while a single articulating component, stem component 126 and fastener 128 are described and shown with respect to the drawings, additional articulating components 122, stem components 126 and fasteners 128 may also be provided that can offer various material characteristics and/or geometric configurations as further discussed herein.

Figure 28:
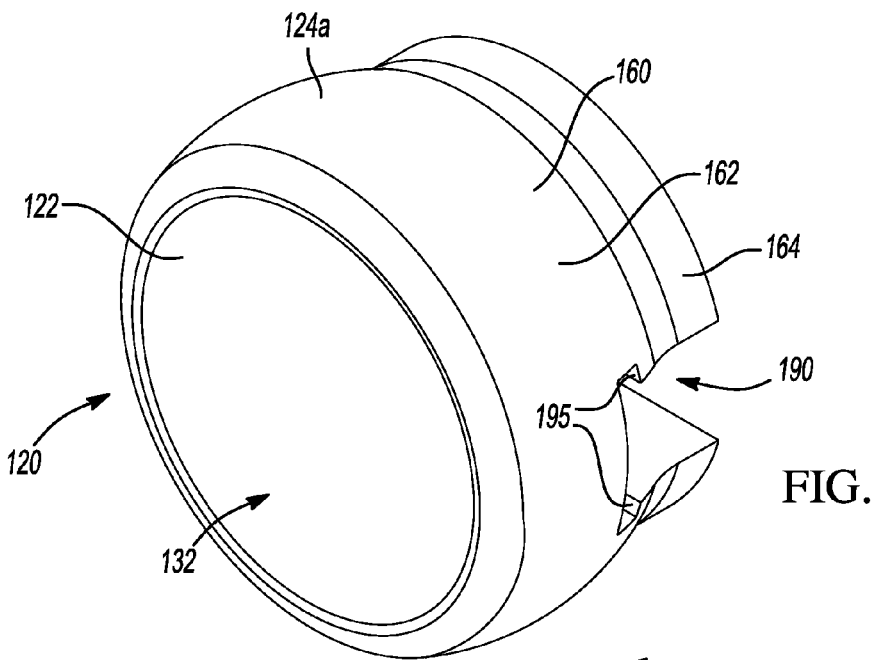
FIG. 28 is a proximal perspective view of an articulation component and head component of a modular radial head prosthesis system according to one example of the present teachings.
Figure 29:
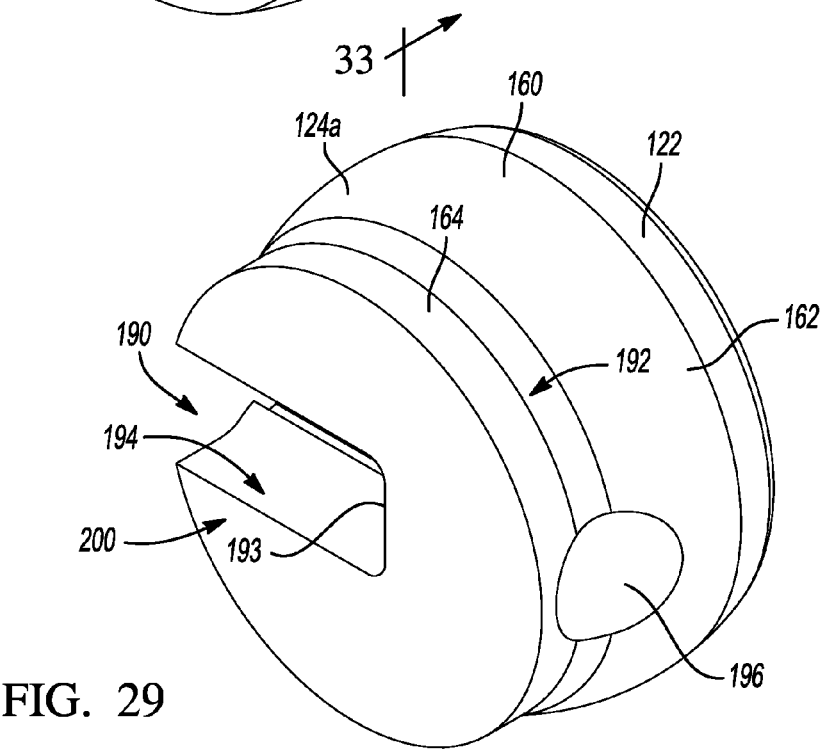
FIG. 29 is a distal perspective view of the articulation component and head component of FIG. 28.
Figure 30:
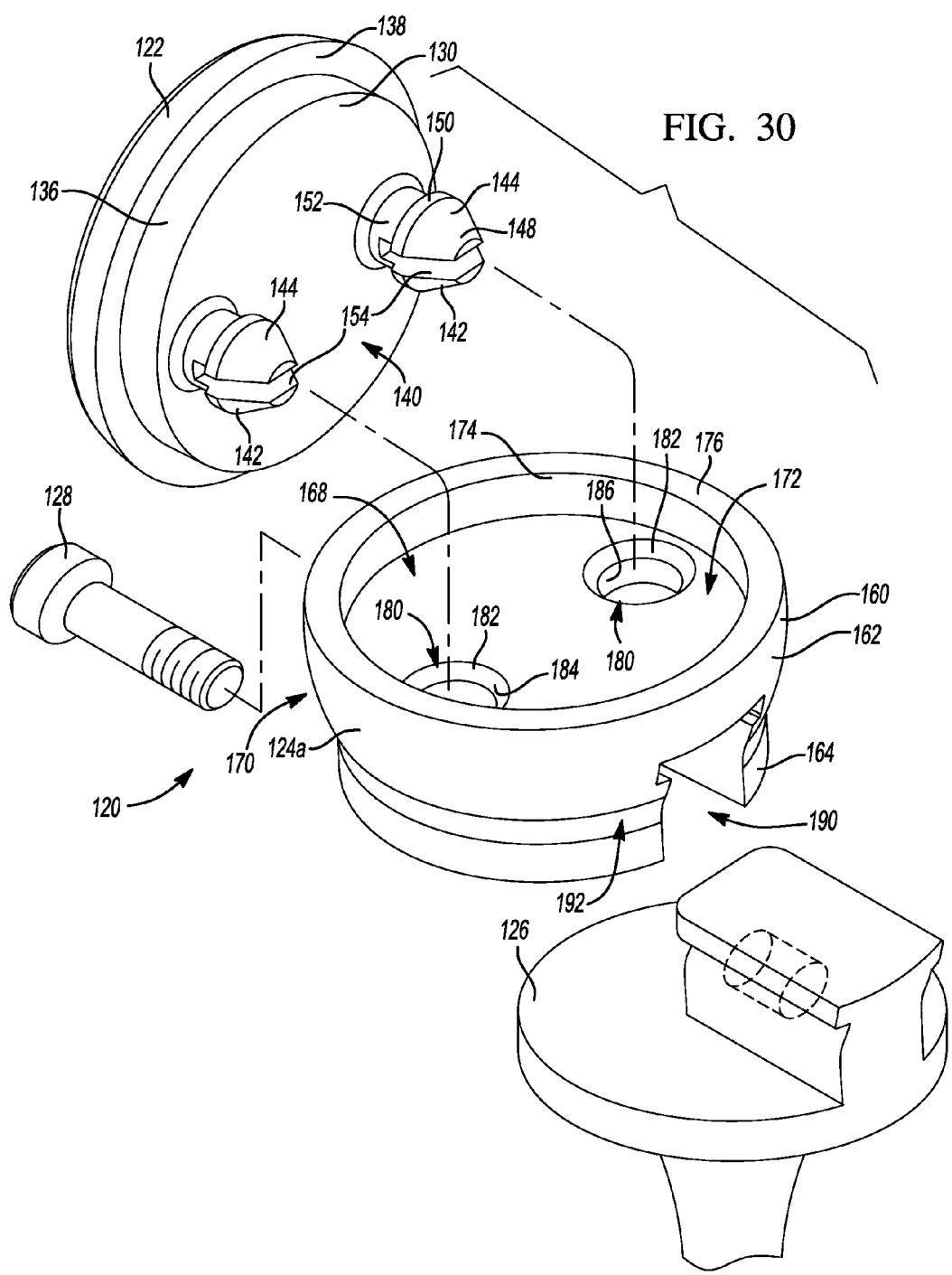
FIG. 30 is an exploded perspective view of the modular radial head prosthesis system of FIGS. 28 and 29 further illustrating a stem component and a fastener.

With particular attention now given to FIGS. 28-30, the articulating component 122 will be described in greater detail. The articulating component 122 can include a body portion 130 that is fashioned to approximate the dimensions of a damaged or removed radial head. Thus, the outer shape is roughly cylindrical, having a slightly concaved top or articulation portion 132 for natural articulation with the capitellum (see reference 39, FIG. 14) or alternatively a capitellar implant. Because the articulating component 122 is the portion of the prosthesis that will articulate with the capitellum 39 upon joint movement, this structure can be constructed of a biologically accepted rigid material. Such a material can include, for example, metal, alloy, PEEK, UHMWPE, or ceramic. If the rigid material is metal or alloy, appropriate materials can include for example, titanium, stainless steel, and cobalt chrome. The articulating component 122 can include a central extension portion 136 and a radial lip 138. In one example, the central extension portion 136 can generally define a cylindrical member that has an outer geometry that substantially matches an outer profile of the articulating component 122, but has a reduced diameter. Depending from a distal surface 140 of the central extension portion 136 are connection portions 142. In the example shown, the connection portions 142 generally take the form of male insertion portions or posts 144 having conical end portions 148 that extend from circumferential extension portions 150. A narrowed neck 152 is formed generally between the distal surface 140 of the central extension portion 136 and the circumferential extension portions 150.

The connection portions 142 can generally define longitudinal channels 154 formed therethrough. As will be described herein, the channels 154 can allow the connection portions 142 to compress radially inwardly during an assembly step. The connection portions 142 are monolithic and formed integral with the remaining structure of the articulating component 122. In other examples, the connection portions 142 can be modular and be formed of distinct material from the remainder of the articulation component 122. While a pair of connection portions 142 are shown and described with respect to the disclosed embodiments, it is appreciated that additional or fewer connection portions 142 may be provided on the articulating component 122. In the particular example shown, a pair of connection portions 142 formed generally toward a perimeter of the distal surface 140 of the central extension portion 136 can provide anti-rotation characteristics in an assembled position as will become appreciated from the following discussion. The connection portions 142 can additionally or alternatively be provided elsewhere on the distal surface 140.

Figure 31:
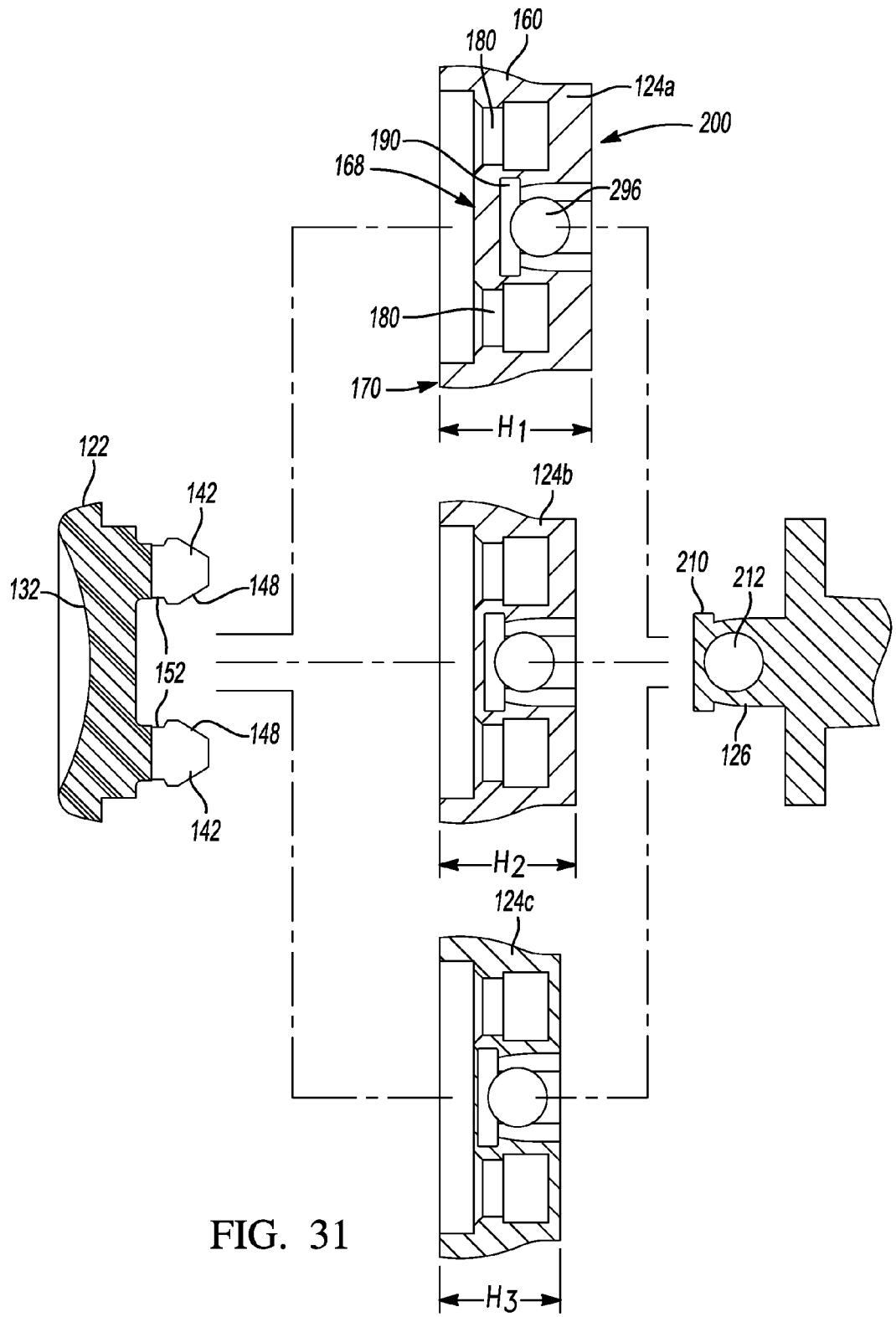
FIG. 31 is an exploded cross-sectional view of the modular radial head prosthesis system illustrating a plurality of head components having different dimensions.

With reference now to FIGS. 28-31, the head component 124*a* will be described in greater detail. For discussion purposes, description of the head component 124*a* will be given, however, it is appreciated that the head components 124*b* and 124*c* shown in FIG. 31 are constructed similarly, but have different dimensions. The head component 124*a* generally comprises a generally cylindrical body 160 that has a generally bulbous proximal portion 162 and a cylindrical distal portion 164. A countersink 168 is formed in a proximal end 170 of the bulbous proximal portion 162. The countersink 168 can generally terminate at a proximal surface 172 and is defined within a cylindrical wall 174. A radial annular rim edge 176 is provided at the proximal end 170.

A pair of connection portions 180 are formed in the cylindrical body 160. In general, the connection portions 180 include female receiving portions or closed bores 182 formed into the proximal surface 172. Each of the female receiving portions 182 generally include an angled beveled entrance surface 184 and a reduced diameter portion 186. As can be appreciated, the connection portions 180 (FIGS. 32A-B) can be provided to interconnect with the connection portions 142 provided on the articulating component 122 to form an intraoperative coupling mechanism 185. In this way, a pair of female receiving portions 182 are formed generally toward a perimeter of the proximal surface 172 to cooperatively align for receipt of the male insertion portions 144 of the articulating component 122. It is appreciated, however, that additional or fewer connection portions 180 may be provided on the cylindrical body 160 of the head component 124*a* as desired. Furthermore, while male insertion portions 144 have been described as associated with the articulating component 122 and female receiving portions 182 have been described in relation to the head component 124*a*, these features may be provided on opposite components or mixed male insertion/female receiving portions.

The head component 124*a* can further include another connection portion in the form of a T-shaped channel 190 having an entrance generally through a sidewall 192 of the cylindrical body 160. As best illustrated in FIG. 29, the T-shaped channel 190 can terminate at an endwall 193 within the cylindrical body 160. Explained differently, the T-shaped channel 190 does not extend completely through the diameter of the head component 124*a*. The T-shaped channel 190 includes opposed arcuate sidewalls 194 and an opposed undercut ledge 195. A counterbore 196 is also formed into the sidewall 192 of the cylindrical body 160. In general, the counterbore 196 can be coaxial with a length defined by the T-shaped channel 190. As shown in FIG. 33, a reduced diameter portion or collar 198 is provided in the cylindrical body 160 generally between the counterbore 196 and the T-shaped channel 190. As shown in FIG. 29, the T-shaped channel 190 can extend through a distal end 200 while the counterbore 196 is provided exclusively on the sidewall 192.

With specific reference now to FIG. 31, the head components 124a, 124b and 124c are shown having various heights measured between respective proximal and distal ends 170 and 200. In general, the connection portions 180 are geometrically consistent between each of the head components 124a, 124b and 124c for selectively interconnecting with the connection portions 142 of the articulating component 122. Again, while the height dimensions are shown having various dimensions between the respective head components 124a, 124b and 124c, other geometrical relationships may be different between the respective head components 124a, 124b and 124c to allow a surgeon to selectively and intraoperatively choose a particular head component that is desired for a given patient's circumstances. The head components 124a, 124b and 124c can be formed from metal or alloy, such as, but not limited to, titanium, stainless steel and cobalt chrome.

The stem component 126 will now be briefly described. The stem component 126 can generally include a stem connection portion in the form of a T-shaped protrusion 210 having a threaded blind bore 212. Again, while one stem component 126 is described and shown in the drawings, it is appreciated that a plurality of stems may be provided (see kit 108, FIG. 27).

An exemplary method of assembling the modular radial head prosthesis system 120 will now be described according to one example. At the outset, once a head component 124a, 124b or 124c has been selected that accommodates the needs of a particular patient, the articulating component 122 can be selected having a particular material depending on the needs of the particular patient, for example, for articulation with a natural bone or a capitellar implant. The articulation component 122 can be attached to the proximal end 170 of the head component (such as 124a). A surgeon can generally align the male insertion portions 144 on the central extension portion 136 of the articulating component 122 for receipt into the complementary female receiving portions 182 provided on the proximal surface 172 of the head component 124a.

With particular reference now to FIGS. 32a and 32b, the male insertion portions 144 are advanced linearly along their axes into the female receiving portions 182. As the conical end portions 148 negotiate across the angled entrance surfaces 184, they compress radially inwardly as they are advanced through the reduced diameter portions 186 of the female receiving portions 182. Once the conical end portions 148 pass beyond the reduced diameter portions 186, the conical end portions 148 retract outwardly to their normal static position. The male insertion portions 144 can snap-fit into the female receiving portions 182. As shown in FIG. 32b, the neck 152 of the male insertion portions 144 is located in an aligned position with the reduced diameter portion 186 while the circumferential extension portion 150 of the male insertion portion 144 is captured by the reduced diameter portion 186. Notably, the central extension portion 136 is configured for receipt into the countersink 168 and the radial lip 138 of the articulating component 122 is configured to rest on the radial edge 176 of the head component 124a.

Figure 34:
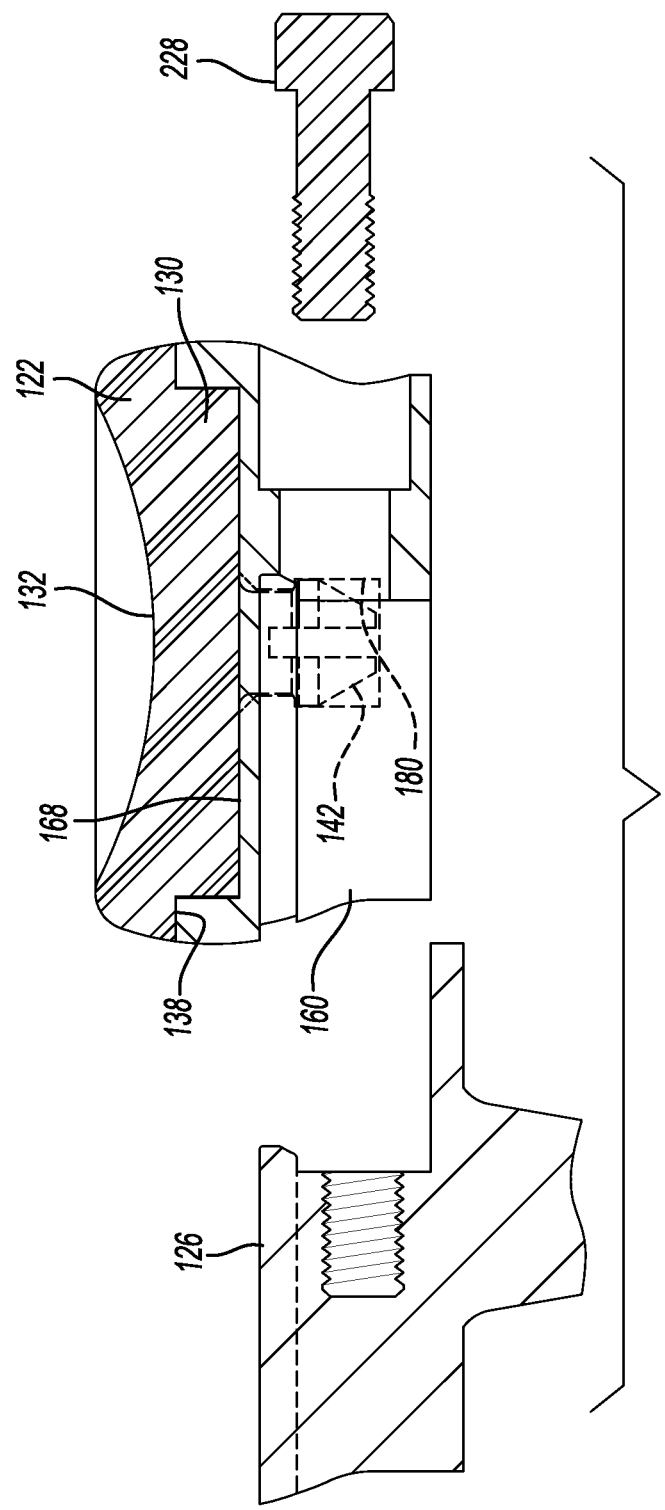
FIGS. 34 and 35 are partial cross-sectional views of the modular radial head prosthesis illustrating an exemplary assembly sequence attaching the stem component.
Figure 35:
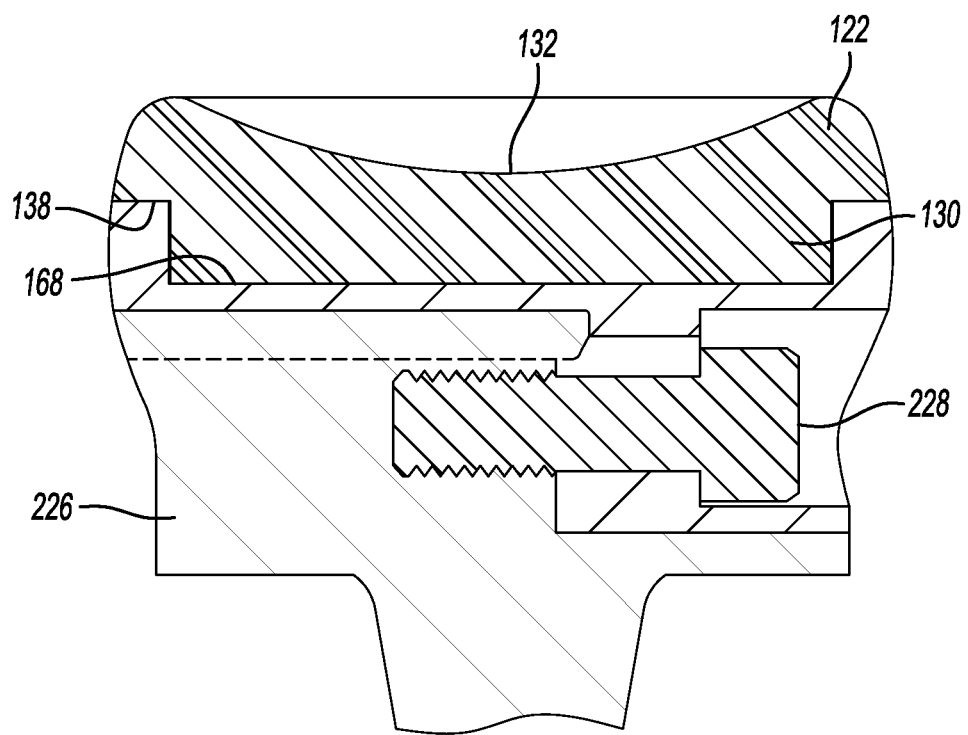

As shown in FIGS. 34-35, the stem component 126 can be operably attached to the head component 124a by slidably advancing the T-shaped protrusion 210 into the complementary shaped T-shaped channel 190 of the cylindrical body 160. The fastener 128 can be advanced into the counterbore 196 formed in the sidewall 192, such that its shank extends through the collar 198 of the cylindrical body 160 and threadably mates with the threaded blind bore 212 of the stem component 126.

Figure 36:
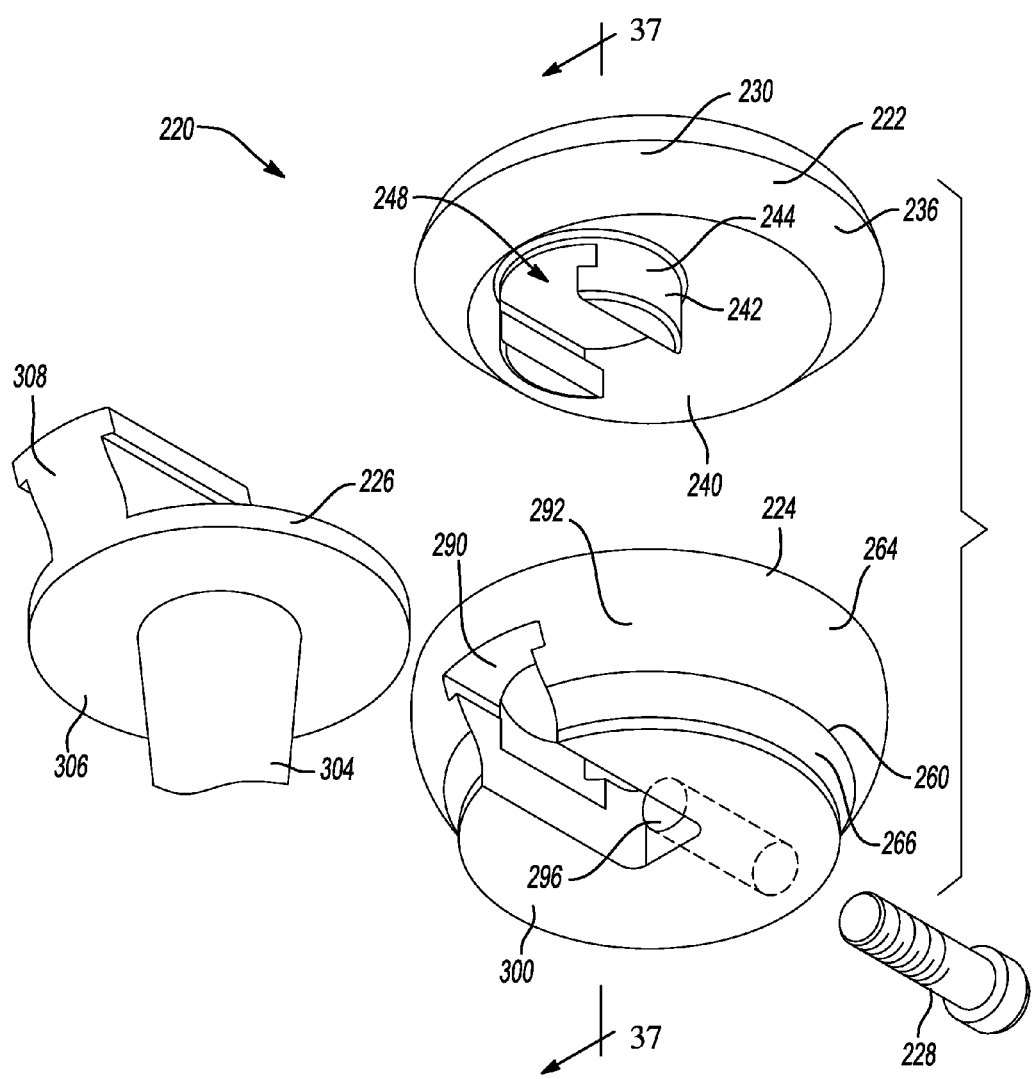
FIG. 36 is an exploded perspective view of a modular radial head prosthesis system constructed in accordance to another example of the present teachings.
Figure 37:
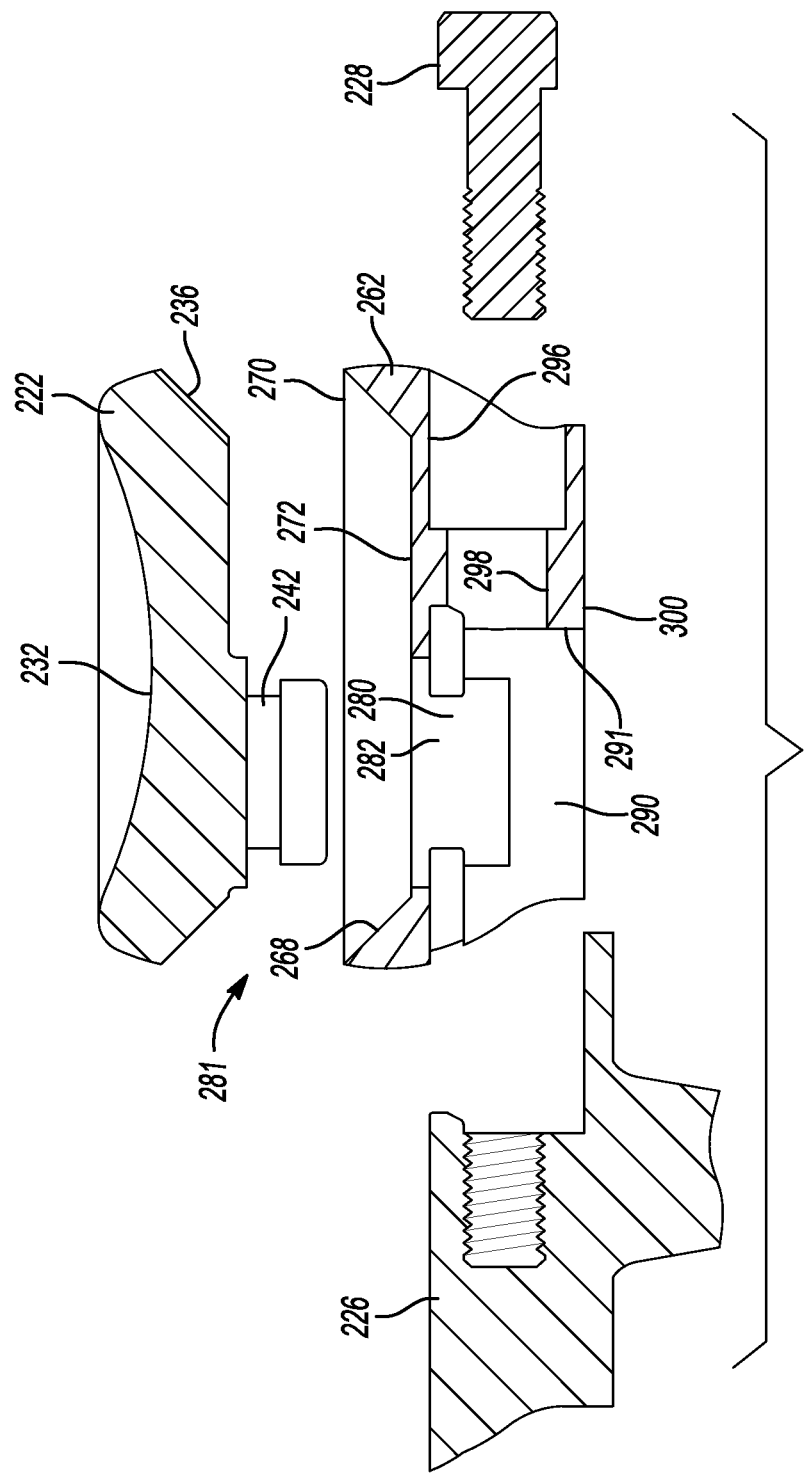
FIGS. 37 and 38 are cross-sectional views of the modular radial head prosthesis system of FIG. 36 illustrating an exemplary assembly sequence.
Figure 38:
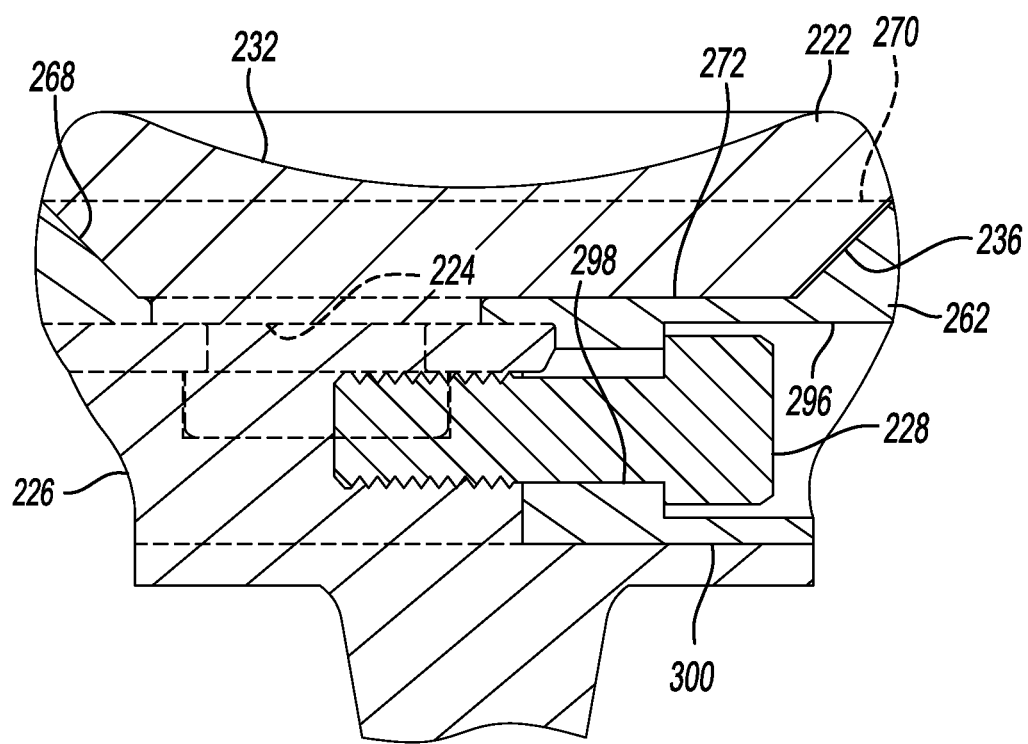
Figure 41:
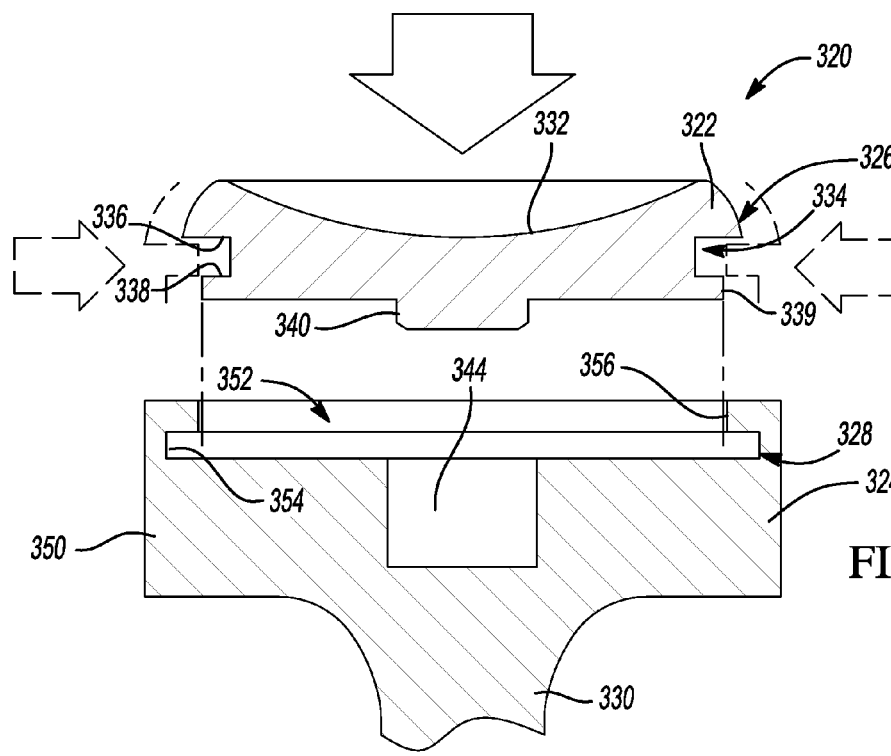
FIG. 41 is a cross-sectional view of the head prosthesis system shown with the articulating component being reduced in size from a first position (phantom line) to a second position (solid line) during an assembly step.

With reference now to FIGS. 36-38, a modular radial head prosthesis system according to another example of the present teachings is shown and generally identified at reference numeral 220. The modular radial head prosthesis system 220 can generally include an articulating component 222, a head component 224, a stem component 226 and a fastener 228. As with the modular radial prosthesis system 120 described above, the modular radial head prosthesis system 220 can be provided in various components as a kit, and having different dimensions for selected components. In this way, the modular radial head prosthesis system 220 can allow a surgeon to use a selected articulating component 222 and choose a desired head component 224 from a plurality of head components and a stem component 226 from a plurality of stem components to satisfy a given patient's particular needs. A series of head components 224 having different dimensions, such as various height dimensions described above with respect to FIG. 31, can be provided. Similarly, various stem components 226 having various height dimensions can be provided.

The articulating component 222 can include a body portion 230 that is fashioned to approximate the dimensions of a damaged or removed radial head. Thus, the outer shape is roughly cylindrical, having a slightly concave articulating portion 232 (FIG. 37) for natural articulation with the capitellum (see reference 39, FIG. 14), or implant. Because the articulating component 222 is the portion of the prosthesis that will articulate with the capitellum 39 upon joint movement, this structure can be constructed of a biologically accepted rigid material. Such a material can include, for example, metal, alloy, PEEK, UHMPWE or ceramic. The articulating component 222 can include an angled extension portion 236 that can generally include a male tapered portion that extends to a distal surface 240. Depending from the distal surface 240 of the extension portion 236 is a connection portion 242. In the example shown, the connection portion 242 generally takes the form of a cylindrical member 244 that extends from a location offset from a center point of the distal surface 240. The cylindrical member 244 can have a T-shaped slot 248 formed therein. In the example shown, the T-shaped slot 248 can extend entirely through the cylindrical member 244. The connection portion 242 is monolithic and formed integrally with the remaining structure of the articulating component 222. Alternatively, the connection portion 242 can be modular and be formed of a distinct material. Because the connection portion 242 is formed at a radially offset location relative to a center point of the distal surface 240, the connection portion 242 can provide anti-rotation characteristics in an assembled position as will become appreciated from the following discussion.

Additional description of the head component 224 will now be described in greater detail. The head component 224 comprises a generally cylindrical body 260 that has a generally bulbous proximal portion 262 and a cylindrical distal portion 266. A countersink 268 is formed on a proximal end 270 of the bulbous proximal portion 262. The countersink 268 can generally include a female tapered wall that has a geometry complementary with the tapered surface of the extension portion 236 of the articulating component 222. The countersink 268 can generally terminate at a proximal surface 272 for engagement with the distal surface 248.

A connection portion 280 (FIG. 37) is formed in the cylindrical body 260. In general, the connection portion 280 can include a female receiving portion 282 formed into the proximal surface 272. The female receiving portion 282 can generally include a geometry that is suitable to receive the cylindrical portion 244 of the connection portion 242 on the articulating component 222. The connection portion 280 of the head component 224 can facilitate alignment for interconnection with the stem component 226 as will be described. The connection portions 242 and 280 can collectively provide an articulation coupling mechanism 281 (FIG. 37). In the example shown, the connection portion 242 of the articulating component 222 is not configured to directly interconnect with the connection portion 280 of the head component 224. Notably, the connection portion 280 on the head component 224 is also offset from a center point of the head component 224 a distance that is compatible for alignment and receipt of the cylindrical portion 244 of the connection portion 242 of the articulating component 222.

The head component 224 can further include another connection portion in the form of a T-shaped channel 290 having an entrance generally through a sidewall 292 of the cylindrical body 260. As illustrated in FIGS. 36-38, the T-shaped channel 290 can terminate at an end wall 291 within the cylindrical body 260. Explained differently, the T-shaped channel 290 does not extend completely through the diameter of the head component 224. A counterbore 296 is also formed into the sidewall 292 of the cylindrical body 260 opposite the T-shaped channel 290. In general, the counterbore 296 can be coaxial with a length defined by the T-shaped channel 290. As best illustrated in FIG. 37, a reduced diameter portion or collar 298 is provided in the cylindrical body 260 generally between the counterbore 296 and the T-shaped channel 290. As illustrated in FIG. 36, the T-shaped channel 290 can extend through a distal end 300 of the cylindrical body 260 while the counterbore 296 is provided exclusively on the sidewall 292.

With particular reference now to FIG. 36, the stem component 226 will be described in greater detail. The stem component 226 can include a longitudinally extending body portion 304, a platform 306 and a stem connection portion in the form of a T-shaped protrusion 308. A threaded blind bore 312 can be provided in the T-shaped protrusion 308 to align with the counterbore 296 for receipt of a fastener.

An exemplary method of assembling the modular radial head prosthesis system 220 will now be described according to one example. At the outset, a surgeon can select a given articulating component 222, a head component 224 and a stem component 226 that provide the desired dimensions, materials, etc. according to a patient's particular needs. Next, the cylindrical member 244 of the connection portion 242 on the articulating component 222 is advanced axially into the connection portion 280 of the head component 224. Next, the T-shaped protrusion 308 on the stem component 226 can be slidably advanced into the T-shaped channel 290 of the head component 224. During the advancement of the T-shaped protrusion 308 on the stem component 226, the T-shaped protrusion 308 will slidably interconnect with the T-shaped channel 290 of the head component 224 as well as the T-shaped slot 248 on the articulating component 222, thereby coupling the articulating component 222, head component 224 and stem component 226 together. In other words, the T-shaped channel 290 and the T-shaped slot 248 are co-aligned channels for receipt of the T-shaped protrusion 308 to simultaneously couple the head 224, the stem 226, and the articulation portion 222. The fastener 228 can then be advanced into the counterbore 296 formed in the sidewall 292, such that its shank extends through the collar 298 of the cylindrical body 260 and threadably mates with the threaded blind bore 312 on the stem component 226.

Turning now to FIGS. 39-42, a modular radial head prosthesis system according to additional features is shown and generally identified at reference numeral 320. The modular radial head prosthesis system 320 can generally include an articulating component 322 and a head component 324. As will be described, the articulating component 322 can be formed of a polymeric material and be reduced in size during an assembly step, such as by placing it in a freezer or exposing it to liquid nitrogen. The articulating component 322 can then be coupled to the head component 324 by locating a first connection portion 326 of the articulating component 322 relative to a second connection portion 328 of the head component 324 and allowing the articulating component 322 to return to ambient temperature causing the first connection portion 326 to interlock with the second connection portion 328. The first connection portion 326 can be a male extension member and the second connection portion 328 can be an undercut annular groove.

In one example, the head component 324 can further include an integrally formed stem portion 330 extending therefrom. In other examples, a modular stem can be provided that mates with the head component 324. According to the present disclosure, the modular radial head prosthesis system 320 can provide a series of head components 324 having different dimensions, such as height dimensions described above with respect to FIG. 31 that can be selectively and alternatively coupled with the articulating component 322. The modular radial head prosthesis system 320 can allow a surgeon to use a selected articulating component 322 and choose a desired head component 324 from a plurality or kit of head components according to a patient's particular needs. As can be appreciated, different head components having different geometries and/or dimensions may be preferred from one patient to the next. As with the other embodiments disclosed herein, in some cases, it may be desired to build up the height of the distal radius depending upon the amount of host radius that is being replaced.

The modularity of the modular radial head prosthesis system 320 can allow a surgeon to have a common articulating component 322 that can be intraoperatively coupled with various head components 320 to create an assembled modular radial head prosthesis that provides the desired geometry and profile for any particular patient. It is also appreciated that while a single articulating component and head component are described and shown with respect to the drawings, additional articulating components 322 may also be provided that can offer various material characteristics and/or geometric configurations as described herein.

The articulating component 322 will now be described in greater detail. The articulating component 322 can include a body portion 330 that is constructed to approximate the dimensions of a damaged or removed radial head. Thus, the outer shape is roughly cylindrical, having a slightly concaved top or articulating portion 332 for natural articulation with the capitellum (see reference 39, FIG. 14) or alternatively a capitellar implant. Because the articulating component 322 is the portion of the prosthesis that will articulate with the capitellum 39 upon joint movement, this structure can be constructed of a biologically accepted rigid material. As identified above, such a material can include, for example, a polymeric material (UHMWPE) but may also include other materials that are suitable for articulation and can provide a reduction in size that allows for assembly of the first and second connection portions 326 and 328 described above.

The articulating component 322 can include the first connection portion 326 that can be in the form of an annular undercut 334. The undercut 334 can have an upper ridge 336 a lower ridge 338 and a lip 339. An extension portion 340 can be formed on one side of the articulating component 322. The extension portion 340 can generally include a cylindrical member that has an outer geometry that substantially matches an outer profile of a cavity 344 defined on the head component 324, but has a reduced diameter. The extension portion 340 can be located offset from a centerpoint of the articulating component 322 to inhibit rotation of the articulating component 322 relative to the head component 324 in an assembled position. In another configuration, the articulating component 322 can be keyed to the head component 324.

The head component 324 can generally comprise a cylindrical body 350 that has a central recess 352. The second connection portion 328 can collectively include an annular groove 354 and an upper ridge 356 formed around the head component 324. The head component 324 can be formed of a metal or metal alloy, such as, but not limited to, titanium, stainless steel and cobalt chrome. It is appreciated that while the first connection portion 326 has been shown and described as part of the articulation component 322 and the second connection portion 328 has been shown and described as part of the head component, the location of these features may be reversed. Furthermore, it is contemplated that other geometries may be alternatively be provided that attain a compression fit between the articulating component 322 and the head component 324.

Figure 42:
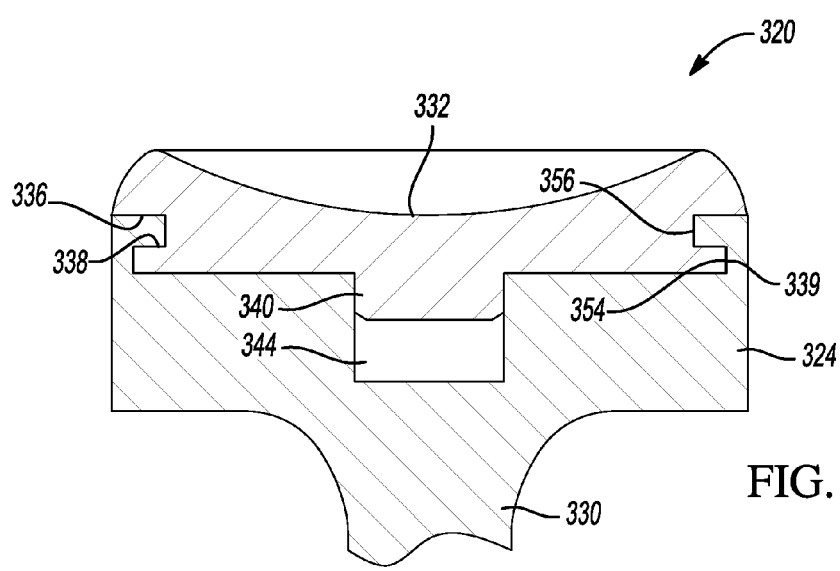
FIG. 42 is a cross-sectional view of the head prosthesis system of FIG. 41 and shown with the articulating component having a compression fit with the head component once the articulating component returns to its original size.

An exemplary method of assembling the modular radial head prosthesis system 320 will now be described according to one example. At the outset, once a head component 324 has been selected that accommodates the particular needs of a given patient the articulating component 322 can also be selected. As further discussed herein, selection of the articulating component 322 and the head component 324 can be based, at least in part, on first determining a distance between a proximal radius and a humerus of the patient. The articulating component 322 can then be shrunk in size. In one example, the articulating component 322 can be exposed to a reduction in temperature, such as by placing it in a freezer or subjecting it to liquid nitrogen. As can be appreciated, by cooling the components, it contracts or shrinks and the reduction in size can allow the outer diameter of the lip 339 to be less than an inner diameter of the ridge 356 on the head component 324. In this regard, the lip 339 of the articulating component can be advanced into the recess 352 of the head component 324. Concurrently, a user can align the extension portion 340 of the articulating component 322 with receipt into the cavity 344 of the head component 324. The upper ridge 336 of the first connection portion 326 can rest on top of the ridge 356 of the second connection portion 328. The articulating component 322 is then allowed to return to ambient temperature (FIG. 42). Returning to ambient temperature, or more specifically body temperature when implanted, allows the lip 339 of the undercut portion 334 to expand and be captured within the groove 354 of the head component 324 as illustrated in FIG. 42. This can result in a compression fit between the articulating component 322 and the head component 324. According to other examples, the head component 324 can additionally or alternatively be subjected to an elevated temperature that causes the inner diameter of the ridge to expand.

The description of the disclosure is merely exemplary in nature and, thus, variations that do not depart from the gist of the disclosure are intended to be within the scope of the disclosure. Such variations are not to be regarded as a departure from the spirit and scope of the disclosure. It is to be understood that the above-described arrangements are only illustrative of the application of the principles of the present disclosure. Numerous modifications and alternative arrangements may be devised by those skilled in the art without departing from the spirit and scope of the present disclosure and the appended claims are intended to cover such modifications and arrangements. Thus, while the present disclosure has been shown in the drawings and fully described above with particularity and detail in connection with what is presently deemed to be the most practical and preferred embodiment(s) of the disclosure, it will be apparent to those of ordinary skill in the art that numerous modifications, including, but not limited to, variations in size, materials, shape, form, function and manner of operation, assembly and use may be made, without departing from the principles and concepts of the disclosure as set forth in the claims.

What is claimed is:

1. A method for implanting a prosthesis system for replacement of a head portion of a proximal radius, comprising:
   determining a distance between a proximal radius and a humerus;
   selecting one of a first head component or a second head component based on the determination, the first and second head components having unique heights;
   connecting the selected first or second head component to an articulation component by inserting a male insertion member formed on one of the articulation component and the selected head component into a female receiving member formed on the other of the articulation component and the selected head component; and
   connecting a stem component to the selected first or second head component by slidably advancing a T-shaped protrusion formed on the stem component into a complementary shaped female slot formed on the male insertion member and aligning the complementary shaped female slot with another complementary shaped female slot formed on the head component.

2. The method of claim 1 wherein connecting the selected head component comprises:
   slidably advancing a T-shaped protrusion formed on the stem component into a complementary shaped female slot formed on the head component.

3. The method of claim 1 wherein inserting the male insertion member into the female receiving member comprises:
   compressing a portion of the male insertion member radially inwardly.

4. The method of claim 1 wherein inserting the male insertion member into the female receiving member comprises:

capturing a circumferential extension portion formed on the male insertion component with a reduced diameter portion formed in the female receiving member.

5. The method of claim 1 wherein connecting the stem component comprises:

extending a fastener into the T-shaped protrusion and into the selected head component.

6. The method of claim 5 wherein extending the fastener into the T-shaped protrusion comprises:

threadably engaging the fastener with the T-shaped protrusion.

\* \* \* \* \*